(12) United States Patent
Butki

(10) Patent No.: US 10,966,750 B2
(45) Date of Patent: Apr. 6, 2021

(54) NEEDLE ASSEMBLY WITH REVERBERATION FEATURE TO FACILITATE ULTRASOUND GUIDANCE OF THE NEEDLE ASSEMBLY

(71) Applicant: Andrew J. Butki, Clarkston, MI (US)

(72) Inventor: Andrew J. Butki, Clarkston, MI (US)

( * ) Notice: Subject to any disclaimer, the term of this patent is extended or adjusted under 35 U.S.C. 154(b) by 398 days.

(21) Appl. No.: 16/115,947

(22) Filed: Aug. 29, 2018

(65) Prior Publication Data
US 2020/0069330 A1    Mar. 5, 2020

(51) Int. Cl.
*A61B 17/34* (2006.01)
*A61B 8/08* (2006.01)

(52) U.S. Cl.
CPC ........ *A61B 17/3403* (2013.01); *A61B 8/0841* (2013.01); *A61B 17/3417* (2013.01); *A61B 2017/3413* (2013.01)

(58) Field of Classification Search
CPC ............ A61B 17/3403; A61B 17/3417; A61B 2017/3413; A61B 8/0841; A61B 2090/3925; A61B 8/0891; A61M 2005/1587; A61M 2005/1588; A61M 5/158; A61M 5/3286; A61M 5/329; A61M 5/427
See application file for complete search history.

(56) References Cited

U.S. PATENT DOCUMENTS

| 4,072,041 A | 2/1978 | Hoffman et al. |
| 4,249,539 A | 2/1981 | Vilkomerson et al. |

(Continued)

FOREIGN PATENT DOCUMENTS

| DE | 3311804 A1 | 10/1984 |
| JP | 5190502 B2 | 4/2013 |

(Continued)

OTHER PUBLICATIONS

G. Reusz, Needle-related ultrasound artifacts and their importance in anaesthetic Practice, British Journal of Anaesthesia, Feb. 23, 2014, pp. 795-802.

(Continued)

*Primary Examiner* — Mark D Remaly
(74) *Attorney, Agent, or Firm* — Howard & Howard Attorneys PLLC

(57) ABSTRACT

A needle assembly positionable within anatomy of a patient under visual guidance from an ultrasound system. The needle assembly includes an elongate body and a sidewall including an inner surface defining a lumen. A reverberation feature may include opposing portions of the inner surface defining a gap shaped differently than and/or sized smaller than an inner diameter of the lumen. The reverberation feature is configured to reverberate an incident wave to produce reflected waves, from which a visual artifact is generated with the ultrasound system. The opposing portions may be disposed at superior and inferior aspects of the sidewall. The reverberation feature may include opposing planar surfaces oriented parallel or inclined relative to a longitudinal axis, and/or opposing arcuate surfaces extending towards the longitudinal axis. Methods of positioning the needle assembly near target anatomy of a patient, for example within a vessel, under visual guidance are disclosed.

19 Claims, 18 Drawing Sheets

(56) References Cited

U.S. PATENT DOCUMENTS

| | | | |
|---|---|---|---|
| 4,308,875 | A | 1/1982 | Young |
| 4,401,124 | A | 8/1983 | Guess et al. |
| 4,434,661 | A | 3/1984 | Miwa et al. |
| 4,932,961 | A | 6/1990 | Wong et al. |
| 4,977,897 | A | 12/1990 | Hurwitz |
| 5,383,466 | A | 1/1995 | Partika |
| 5,759,154 | A | 6/1998 | Hoyns |
| 5,769,795 | A | 6/1998 | Terwilliger |
| 6,217,518 | B1 | 4/2001 | Holdaway et al. |
| 7,470,232 | B2 | 12/2008 | Hoctor et al. |
| 8,348,847 | B2 | 1/2013 | Vezina |
| 8,414,495 | B2 | 4/2013 | Halmann et al. |
| 8,747,318 | B2 | 6/2014 | Shiina et al. |
| 8,852,103 | B2 | 10/2014 | Rothberg et al. |
| 9,445,837 | B2 | 9/2016 | Fulton, III |
| 2009/0131790 | A1* | 5/2009 | Munrow ............. A61B 8/4488 600/439 |
| 2013/0102899 | A1 | 4/2013 | Vezina |
| 2015/0051489 | A1 | 2/2015 | Caluser et al. |
| 2018/0046875 | A1 | 2/2018 | Caluser |

FOREIGN PATENT DOCUMENTS

| | | |
|---|---|---|
| KR | 101095466 B1 | 12/2011 |
| WO | 0187177 A1 | 11/2001 |
| WO | 2016081023 A1 | 5/2016 |
| WO | 2016148882 A1 | 9/2016 |
| WO | 2017109080 A1 | 6/2017 |

OTHER PUBLICATIONS

B. Braun Medical, Inc., Introcan Safety Family of Peripheral IV Catheters, https://www.bbraunusa.com/en/products-and-therapies/infusion-therapy/iv-vascular-and-admixture/introcan-safety.html#, 2018, pp. 1-11.

G.A. Chapman, Visualisation of needle position using ultrasonography, Anaesthesia, 2006, 61, pp. 148-158.

Frantz J. Gibbs, MD, Ultrasound Guidance for Central Venous Catheter Placement, Gibbs & Murphy: Ultrasound-Guided CVC Placement, www.turner-white.com, Mar. 2006, pp. 23-31.

Winsberg, Use of an acoustic transponder for US visualization of biopsy needles, Department of Radiology, Mount Sinai Medical Center, City University of New York, NY, Sep. 1991, 180(3), 877-8.

Xia, Ultrasonic Needle Tracking with a Fibre-Optic Ultrasound Transmitter for Guidance of Minimally Invasive Fetal Surgery, Europe PMC Funders Group, Med Image Comput Assist Interv, Sep. 2017, 10434, 637-645.

English language abstract and machine-assisted English translation for JP 5190502 extracted from espacenet.com database on Dec. 13, 2018, 15 pages.

English language abstract and machine-assisted English translation for KR 101095466 extracted from espacenet.com database on Dec. 13, 2018, 14 pages.

English language abstract for DE 3311804 extracted from espacenet.com database on Jun. 5, 2018, 23 pages.

\* cited by examiner

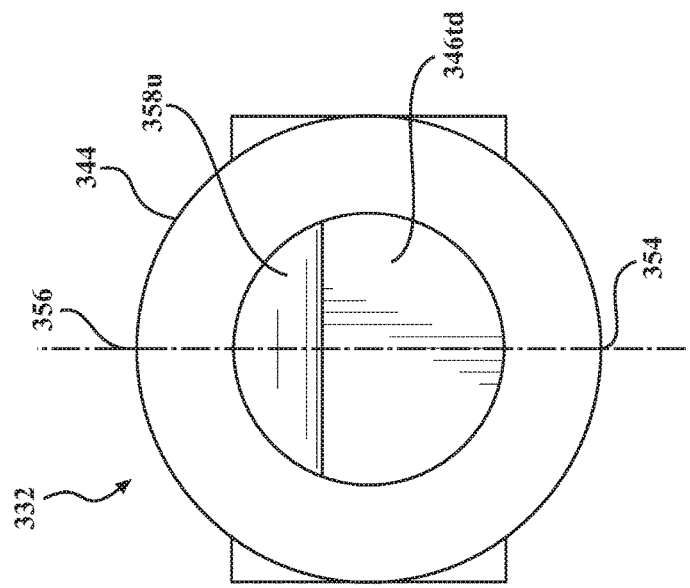
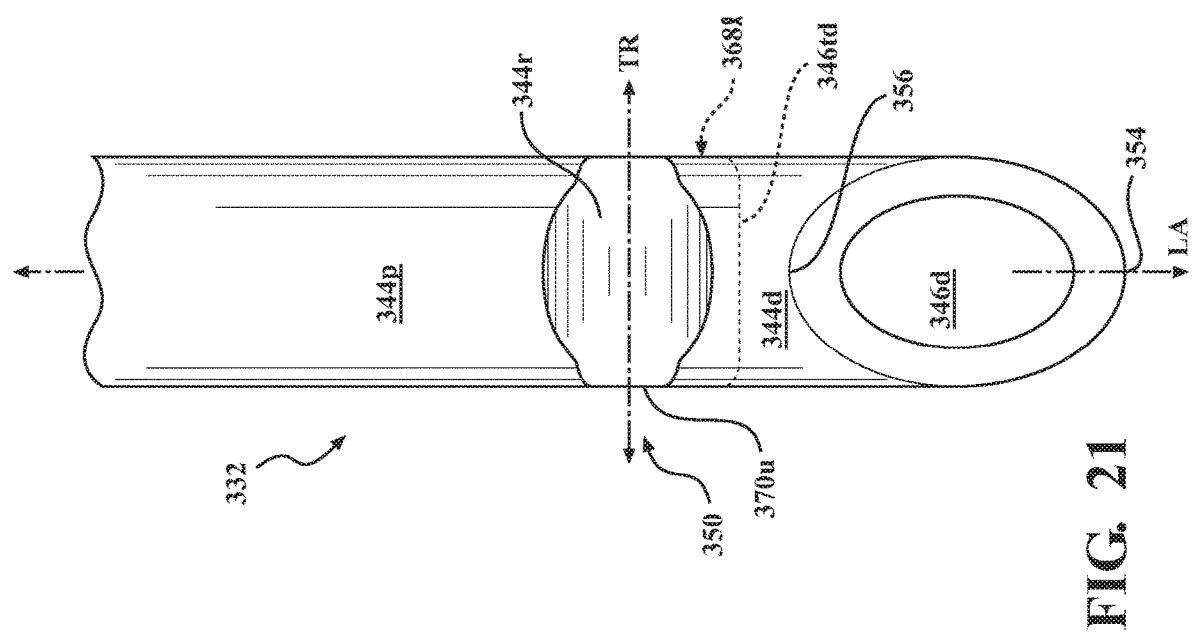

US 10,966,750 B2

NEEDLE ASSEMBLY WITH REVERBERATION FEATURE TO FACILITATE ULTRASOUND GUIDANCE OF THE NEEDLE ASSEMBLY

BACKGROUND

Percutaneous needle placement is a routine task performed in associated with any number of medical procedures, for example therapy delivery, joint aspiration (arthrocentesis), tissue collection (biopsy), and the like. Of particular interest is vascular access, or obtaining access to a vessel (e.g., vein or artery) for the purpose of intravenous (IV) therapy or blood sampling. Typically, the IV placement of the needle relies on the skill and expertise of the treating medical professional to ensure adequate access while avoiding injury to the surrounding structures. For any number of reasons, IV access may be difficult, for example, inexperience of the treating medical professional and/or unreliable, hidden, collapsed, fragile veins, a phenomena known as difficult venous access (DVA).

Ultrasound guidance is becoming increasingly common in the IV placement of a needle assembly. An ultrasound system includes an ultrasound device, for example a handheld probe, which directs incident waves and receives waves reflected from structures internal to the patient anatomy. Based on assumptions of the speed of sound within tissue, the time delay of the reflected waves are used to create a two-dimensional image of the patient anatomy. FIG. 1 shows the placement of a needle assembly 20 under guidance from an ultrasound device 22 using an "out of plane" technique utilized to view the needle in cross section, and FIG. 2 shows an exemplary output of a display of an ultrasound system. In particular, FIG. 2 shows the cross section of the needle assembly 20, and cross sections of a vein (V) and an artery (A).

It is of critical importance to identify the location of the tip of the needle assembly 20 as it is advancing within the patient anatomy. The known needle assembly of FIGS. 1 and 2, however, is indifferent to this consideration, as it is not specifically identifiable of where along a shaft of the needle assembly 20 is intersecting the incident wave of the ultrasound device 22. As a result, the known arrangement again relies on the skill and expertise of the treating medical professional to coordinate positions of the needle assembly 20 and the ultrasound device 22. Moreover, the representation of the cross section of the needle assembly 20 is often faint or otherwise difficult to visualize due to a variety of factors.

The needle assembly 20 is typically percutaneously advanced at an angle of approach, identified as $\theta$ in FIG. 1. With shallower angles of approach, the ultrasound waves reflected from the needle assembly 20 may be generally satisfactory for visualization; however, visualization is less reliable as the angle of approach becomes greater (i.e., steeper).

A known solution is to include removed material (e.g., etchings or indentations) within a sidewall of a needle body having a smooth tubular lumen. For example, U.S. Pat. Nos. 4,401,124 and 9,445,837 disclose features including removed material that purportedly increases the reflectivity of the ultrasound waves. The features require particularly complex geometries, and the reflectivity remains suboptimal at various angles of approach.

Therefore, a need exists in the art for a needle system and methods of positioning a needle assembly within the patient anatomy under visual guidance from the ultrasound system that overcome one or more of the aforementioned disadvantages.

BRIEF DESCRIPTION OF THE DRAWINGS

Advantages of the present disclosure will be readily appreciated as the same becomes better understood by reference to the following detailed description when considered in connection with the accompanying drawings.

FIG. 21 is a top plan view of the needle assembly of FIG. 20.

FIG. 22 is an axial view of the needle assembly of FIG. 20.

SUMMARY

Figure 1:
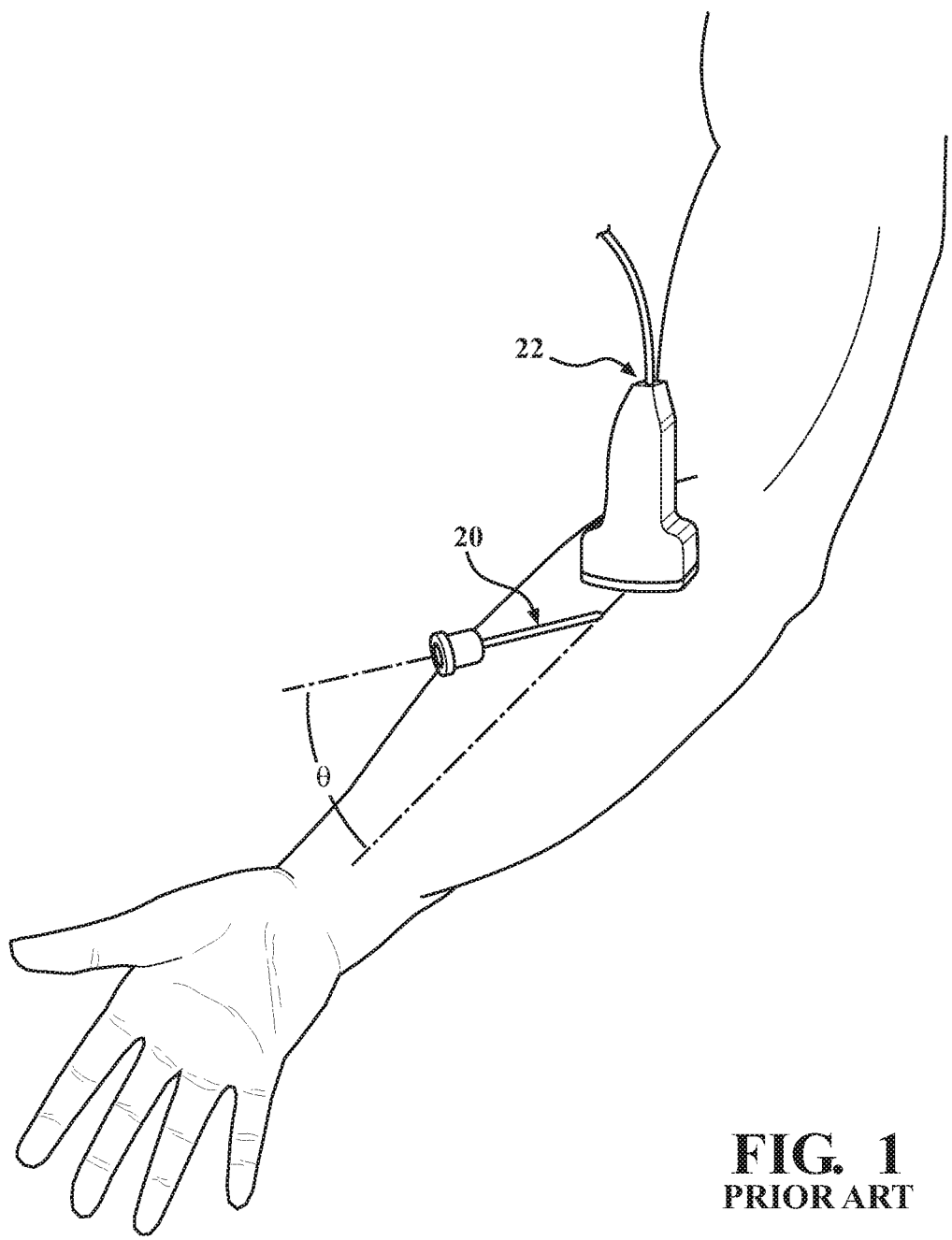
FIG. 1 is a schematic representation of a known needle assembly being percutaneously placed under guidance from an ultrasound device.
Figure 2:
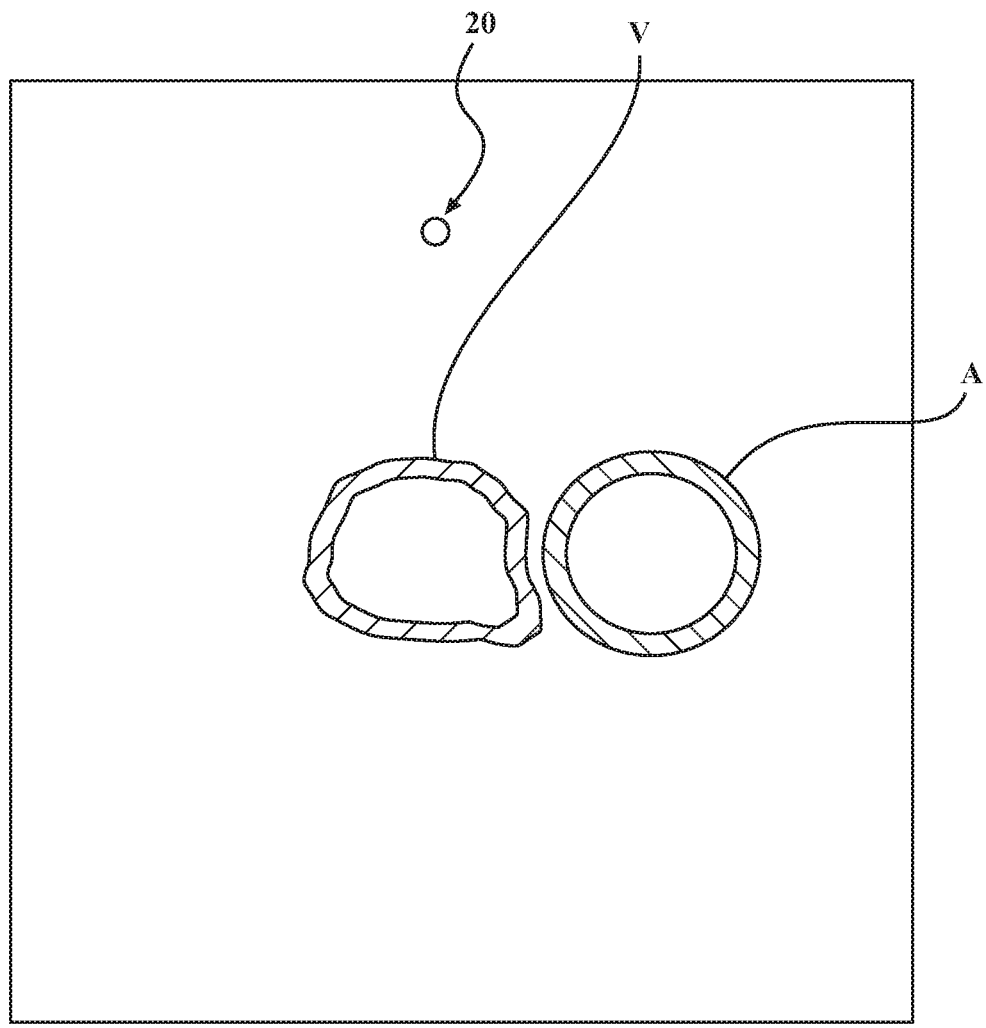
FIG. 2 is a display of an ultrasound system illustrating the output of positioning the known needle assembly of FIG. 2.

According to certain aspects of the present disclosure, a needle assembly is positionable within anatomy of a patient under visual guidance from an ultrasound system. The needle assembly includes an elongate body having a distal end and a proximal end opposite the distal end. The proximal and distal ends define a longitudinal axis of the elongate body. A sidewall extends between the proximal and distal ends. The sidewall includes an outer surface opposite an inner surface defining a lumen. At least a portion of the lumen includes an inner diameter. The elongate body includes a reverberation feature disposed between the proximal and distal ends. The reverberation feature includes opposing portions of the inner surface of the sidewall defining a gap smaller than the inner diameter of the lumen. The reverberation feature is configured to reverberate an incident wave between the opposing portions to produce reflected waves. The ultrasound system is configured to generate a visual artifact in response to receiving the reflected waves to facilitate the visual guidance.

According to certain aspects of the present disclosure, a needle assembly includes an elongate body having a beveled tip. The beveled tip defines a distal end of the elongate body and configured to penetrate the anatomy of the patient. The beveled tip includes a point defining an inferior aspect of the elongate body, and a heel defining a superior aspect of the elongate body. The elongate body further includes a proximal end opposite the distal end. The distal and proximal ends define a longitudinal axis of the elongate body. The elongate body includes a sidewall extending between the beveled tip and the proximal end. The sidewall includes an outer surface opposite an inner surface defining a lumen. At least a portion of the lumen includes an inner diameter. A reverberation feature includes an upper portion of the inner surface at the superior aspect and a lower portion of the inner surface at the inferior aspect to define a gap shaped differently than the lumen. The upper and lower portions are configured to cooperate to reverberate an incident wave to produce reflected waves. The ultrasound system is configured to generate a visual artifact in response to receiving the reflected waves to facilitate the visual guidance.

According to certain aspects of the present disclosure, a method of positioning a needle assembly within a target anatomy of a patient under visual guidance from an ultrasound system is provided. The needle assembly includes an elongate body, a beveled tip, a sidewall defining a lumen, and a reverberation feature comprising opposing portions of an inner surface of the sidewall defining a gap shaped differently than the lumen. The beveled tip is penetrated through overlying skin surface to direct the needle assembly towards the target anatomy at an angle of approach relative to the overlying skin surface. A probe is positioned external to the overlying skin surface at a location above the target anatomy. The probe is operated to direct an incident wave through the overlying skin surface and towards the target anatomy. At least one of the needle assembly and probe is manipulated such that the incident wave is reverberated with the reverberation feature to generate reflected waves. A visual artifact is viewed generated with the ultrasound system based on the reflected waves is viewed on a display.

DETAILED DESCRIPTION

FIGS. 3-10 show a needle assembly 30 in accordance with an exemplary embodiment of the present disclosure. The needle assembly 30 includes an elongate body 32, and in certain embodiments an overlying sheath 34 to be described. The elongate body 32 includes a distal end 36 and a proximal end 38 opposite the distal end 36. The proximal end 38 may extend distally from a hub 40 shown generically in FIG. 3. The hub 40 may be configured coupled to another proximal component (not shown) of the needle assembly 30, for example, a needle safety device, a syringe, a vacuum collection tube, and the like. The elongate body 32 may be rigidly or removably coupled to the hub 40.

Figure 4:
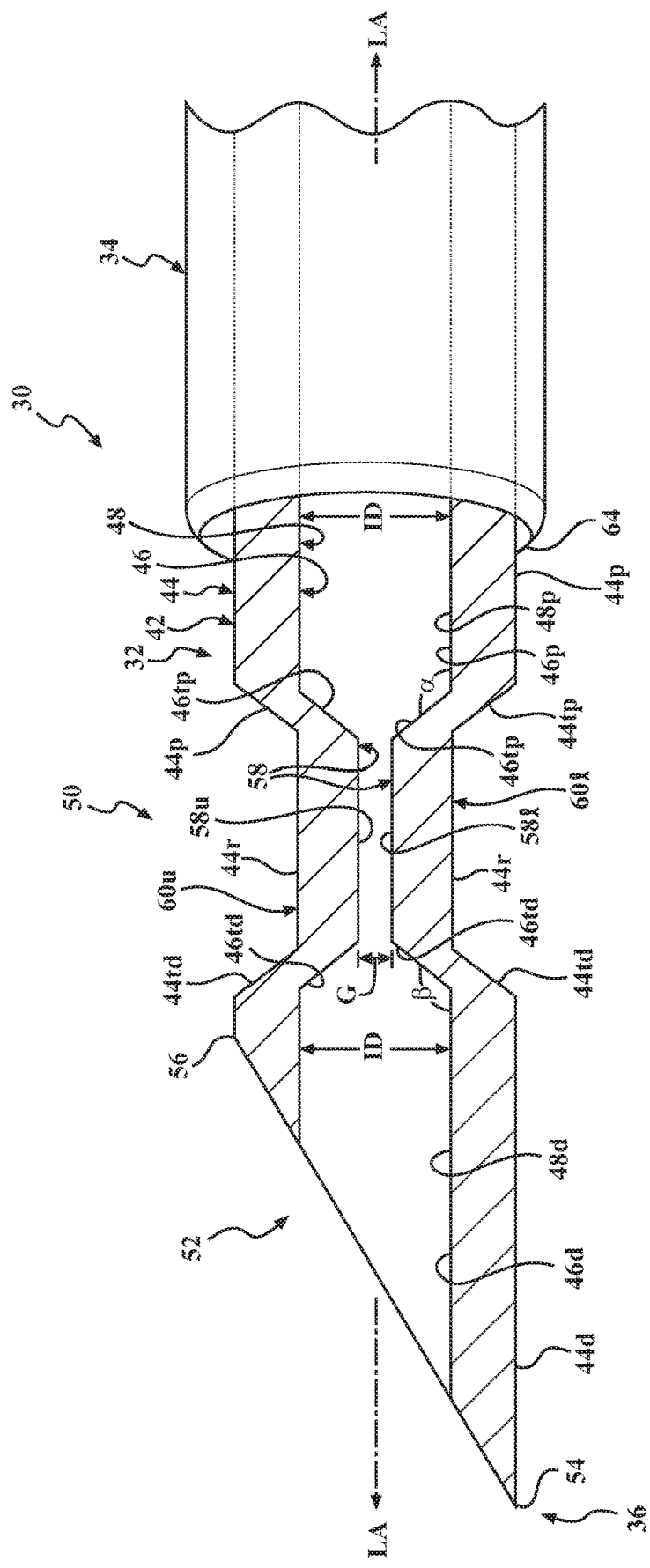
FIG. 4 is a detailed view of the needle assembly of FIG. 3 within rectangle 4-4.

The distal end 36 and the proximal end 38 may define a longitudinal axis (LA) of the elongate body 32, as best shown in FIG. 4. The elongate body 32 includes at least one sidewall 42 extending between the distal and proximal ends 36, 38. The sidewall 42 includes an outer surface 44, and an inner surface 46 opposite the outer surface 44. The inner surface 46 defines a lumen 48 of the elongate body 32. The outer surface 44 may be associated with an outer diameter and the inner surface 46 associated with an inner diameter such that the elongate body 32 is substantially tubular in shape (other than a reverberation feature 50 to be described). Further, the inner and outer surfaces 44, 46 may be oriented parallel to the longitudinal axis (LA) such that the elongate body 32 is substantially straight and tubular in shape. It is contemplated that, in certain variants, the elongate body 32 may be of any suitable cross sectional shape (e.g., triangular, square, rectangular, or a higher-order polygon) and/or include a distal portion curved or angled relative to the longitudinal axis (LA). It is further contemplated that, in certain variants, particularly those with the overlying sheath 34, a portion of the elongate body 32 may be solid in axial section with the exception of the reverberation feature 50. For example, portions proximal and distal to the reverberation feature 50 may be solid in construction.

A beveled tip 52 may define the distal end 36 of the elongate body 32. The beveled tip 52, as appreciated in the art, is configured to penetrate the anatomy of the patient. With concurrent reference to FIGS. 5 and 6, the beveled tip 52 may include a point 54 defining an inferior aspect of the elongate body 32. In other words, the inferior aspect is a bottom of the elongate body 32 when oriented in the manner shown in FIGS. 3 and 4. Likewise, the beveled tip 52 may include a heel 56 defining a superior aspect of the elongate body 32, or a top of the elongate body 32 when oriented in the manner shown in FIGS. 3 and 4. The sidewall 42 extends between the beveled tip 52 and the proximal end 38.

Figure 6:
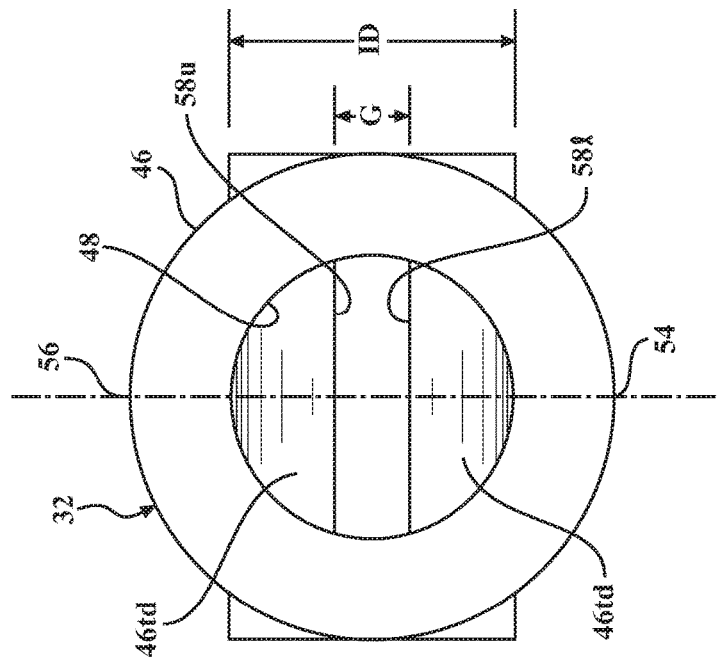
FIG. 6 is an axial view of the needle assembly of FIG. 3.
Figure 5:
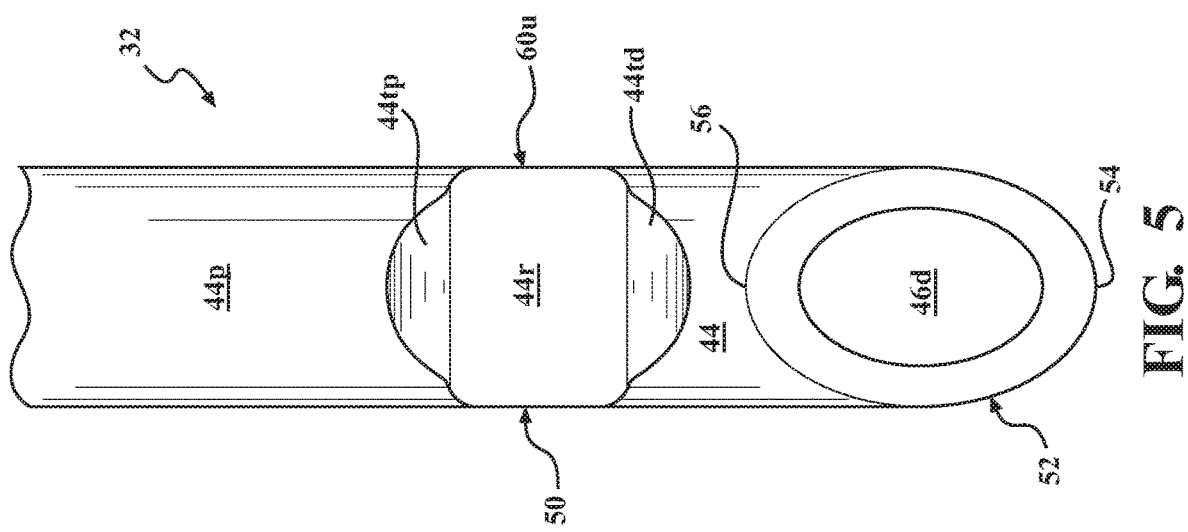
FIG. 5 is a top plan view of the needle assembly of FIG. 3.

The elongate body 32 of the needle assembly 30 includes the reverberation feature 50 disposed between the proximal and distal ends 36, 38. In a manner to be described in detail, the reverberation feature 50, in a broadest sense, is configured to reverberate the incident wave from the ultrasound device 23 (see FIG. 20) to produce the reflected waves. As used herein, the term "reverberate" means to reflect the wave(s) (the incident wave(s) and/or one or more of the reflected waves) at least twice as an echo. With reference to FIGS. 4-6, the reverberation feature 50 may include opposing portions 58 of the inner surface 46 of the sidewall 42 defining a gap (G) shaped differently than the inner surface 46 and/or sized smaller than the inner diameter (ID) of the lumen 48. According to one construction, the term "shaped differently" includes an axial sectional profile of the gap (G) defined by a boundary separate than a boundary defined by the inner surface 46 of the sidewall 42. The lumen 48 extending through the elongate body 32 may be defined by at least two portions, including a proximal lumen portion 48p defined by a proximal inner surface portion 46p and a distal lumen portion 48d defined by a distal inner surface portion 46p, as shown in FIG. 4. The gap (G) defined between the opposing portions 58 may axially separate and be in fluid communication with the proximal and distal lumen portions 48p, 48d.

With continued reference to FIG. 4, the inner surface 46 includes the proximal inner surface portion 46p defining the proximal lumen portion 48p that is tubular in shape. The inner surface 46 may further include at least one proximal transition inner surface portion 46tp extending inwardly or towards the longitudinal axis (LA) relative to the proximal inner surface portion 46p. The illustrated embodiment shows two proximal transition inner surface portions 46tp, one associated with the superior aspect of the elongate body 32 and another associated with the inferior aspect of the elongate body 32. FIG. 4 shows the proximal transition inner surface portion 46tp defining an obtuse angle, α, relative to the proximal inner surface portion 46p. The angle α may be between 95 and 175 degrees, and more particularly between 100 and 150 degrees, and even more particularly between 105 and 125 degrees. The opposing portions 58 extend distally from the proximal transition inner surface portions 46tp. The opposing portions 58 may be opposing planar surfaces oriented parallel to one another to define the gap (G). The arrangement results in the gap (G) being rectangular in axial section and thus shaped differently than the lumen 48 being cylindrical in axial section, as best shown in FIG. 6. In the illustrated embodiment, the opposing planar surfaces are further oriented parallel to the longitudinal axis (LA) of the elongate body 32. In other words, the gap (G) defined between the opposing planar surfaces may be bifurcated by the longitudinal axis (LA), and/or a midline defined between the opposing planar surfaces may be collinear with the longitudinal axis (LA). Extending distally from the opposing portions 58 may be at least one distal transition inner surface portion 46td (also shown in the axial view of FIG. 6). The distal transition inner surface portions 46td extends outwardly or away from the longitudinal axis (LA) of the elongate body 32. The distal transition inner surface portions 46td may be equal in length to the proximal transition inner surface portions 46tp such that the inner diameters of the distal and proximal lumen portions 48p, 48d are equal. The distal inner surface portion 46d may extend distally from the distal transition inner surface portions 46td. FIG. 4 shows the distal inner surface portion 46d defining an obtuse angle, β, relative to the distal transition inner surface portions 46td. The angle β may be between 95 and 175 degrees, and more particularly between 100 and 150 degrees, and even more particularly between 105 and 125 degrees. The angle β may be equal to the angle α. The distal inner surface portion 46d may defined at least a portion of the beveled tip 52.

With the elongate body 32 oriented as shown in FIGS. 4 and 6, the opposing portions 58 of the reverberation feature 50 may include an upper portion 58u at the superior aspect and a lower portion 58l and the inferior aspect. The orientation of FIGS. 4 and 6 may be a preferred orientation of the elongate body 32 as it is percutaneously directed toward target anatomy of the patient based on the structure and function of the beveled tip 52. The arrangement of the upper and lower portions 58u, 58l may be substantially perpendicular to the incident wave(s) being directed from the ultrasound device 23 to facilitate the ultrasound guidance, as to be described in detail.

The outer surface 44 may be contoured to the inner surface 46 to define the sidewall 42 of substantially constant thickness. For example, FIGS. 4 and 5 show the outer surface 44 including a proximal portion 44p, a proximal transition portion 44tp, reverberation portions 44r corresponding to the opposing portions 58, a distal transition portion 44td, and a distal portion 44d. The outer surface 44 being contoured to the inner surface 46 may result in one or more crimps 60, more specifically an upper crimp 60u and a lower crimp 60l. The upper crimp 60u may be defined between the upper portion 58u of the inner surface 46 and one of the reverberation portions 44r of the outer surface 44, and the lower crimp 60l may be defined between the lower portion 58l of the inner surface 46 and the other one of the reverberation portions 44r of the outer surface 44. The crimps 60 of the illustrated embodiment are axially aligned along the longitudinal axis (LA) to define the gap (G). The top plan view of FIG. 5 shows the contour of the outer surface 44 including the upper crimp 60u.

Figure 3:
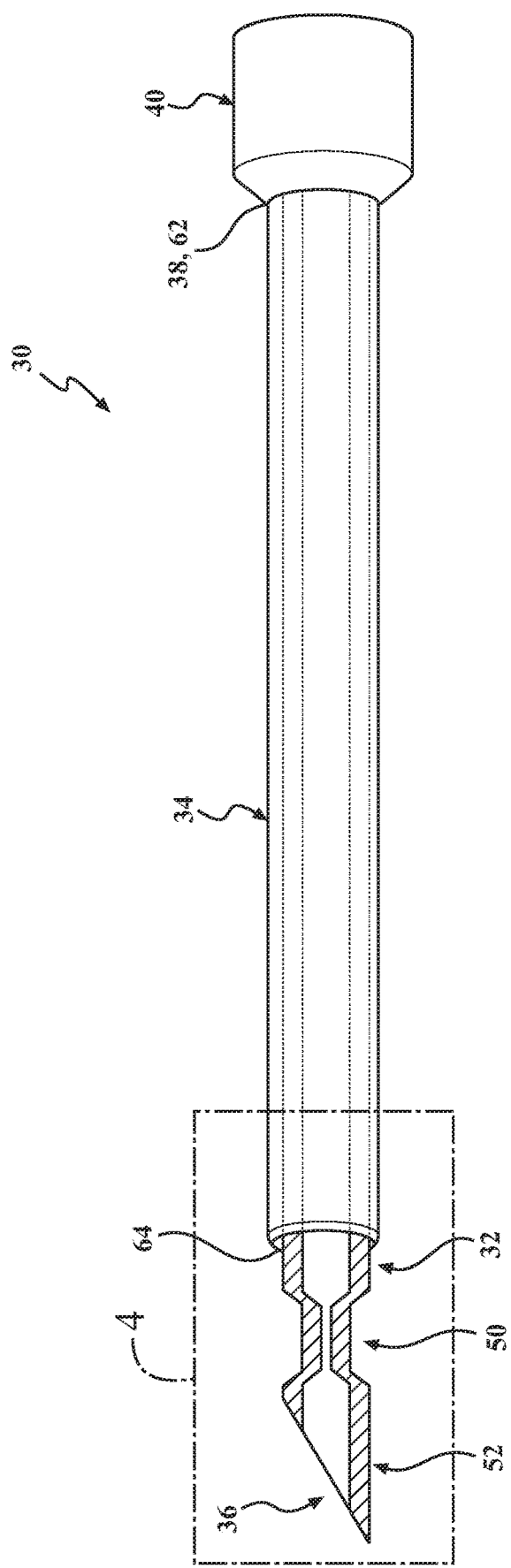
FIG. 3 is a side elevation view of a needle assembly in accordance with an exemplary embodiment of the present disclosure. An elongate body of the needle assembly is shown in section.

As mentioned, it is desirable to identify the location of the distal end 36 of the needle assembly 30 as it is being advanced within the patient anatomy. The reverberation feature 50 is consequently positioned at or near the distal end 36 of the elongate body 32. FIGS. 3-5 best show the reverberation feature 50 positioned immediately proximal to the beveled tip 52. In particular, there is a minimal distance between the heel 56 of the beveled tip 52 and the transition portions 44td, 46td defining a portion of the reverberation feature 50. It is appreciated that the reverberation feature 50 may be positioned at any suitable location between the proximal and distal ends 36, 38 of the elongate body 32. Further, in embodiments including the overlying sheath 34, the sheath 34 may include a proximal end 62 and a distal end 64, as shown in FIG. 3. The distal end 64 of the sheath 34 may be axially positioned proximal to the reverberation feature 50. Among other advantages, the arrangement prevents interference of the reflected waves with the sheath 34 as the ultrasonic waves are returning or moving towards the ultrasound device 23.

Figure 9:
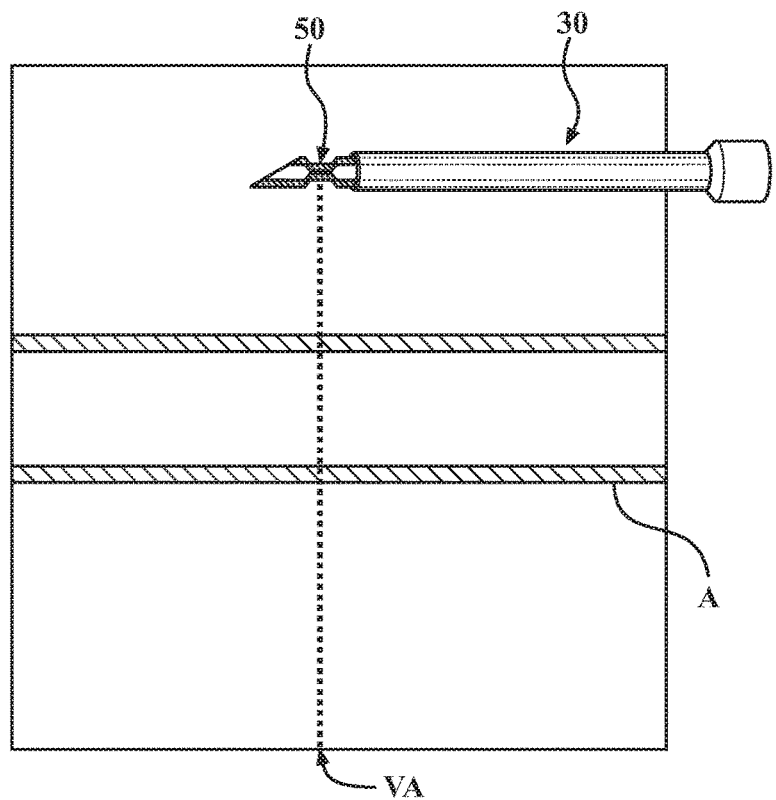
FIG. 9 is a representation of the display of the ultrasound system showing the artifact of FIG. 8 in relation to a side elevation view of the needle assembly and vein.
Figure 10:
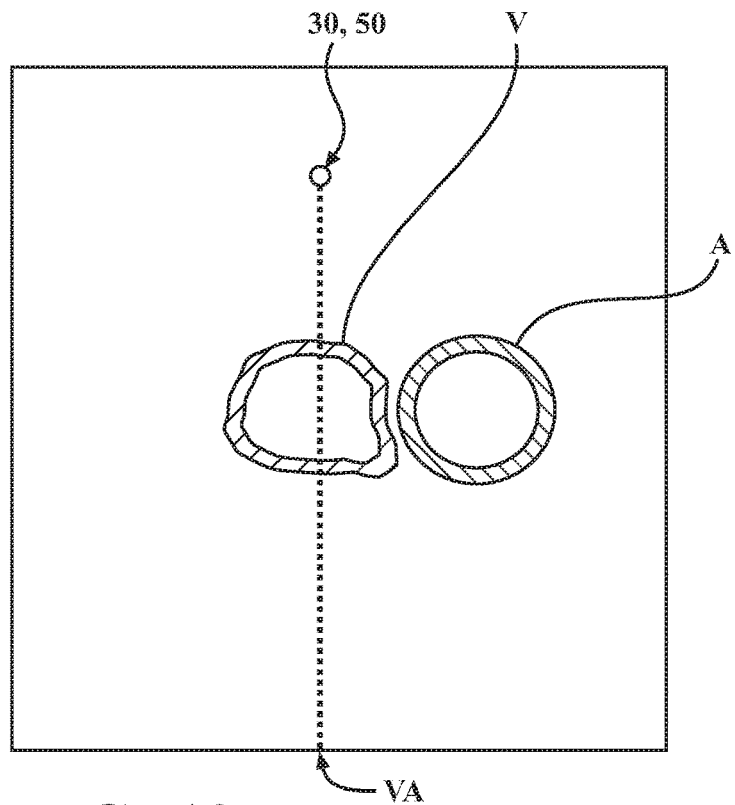
FIG. 10 is a representation of the display of the ultrasound system showing the visual artifact of FIG. 8 in relation to an axial view of the needle assembly and vein.

Operation of the reverberation feature 50 will now be described with reference to FIGS. 7-10. With the needle assembly 30 positioned near the target anatomy, for example superior to the vein (V) as shown in FIGS. 9 and 10, the ultrasound device 23 is operated to direct the incident wave (*) through the target anatomy and the needle assembly 30 positioned therein. While represented as a ray, it should be appreciated that the incident wave (*) may be a two-dimensional beam (B) and its subsequent reverberations (a, b, c, . . . ) may be two-dimensional beams oriented based on the orientation of the ultrasound device 23; e.g., whether an "in plane" or the aforementioned "out of plane" technique is being utilized. The elongate body 32 may be oriented as shown in FIGS. 4 and 6 such that the point 36 of the beveled tip 52 penetrates the anatomy. In such an orientation and depending on an angle of approach θ of the needle assembly 30 and a position of the ultrasound device 22, the opposing portions 58 may be oriented substantially perpendicular to the incident wave (*).

Figure 7:
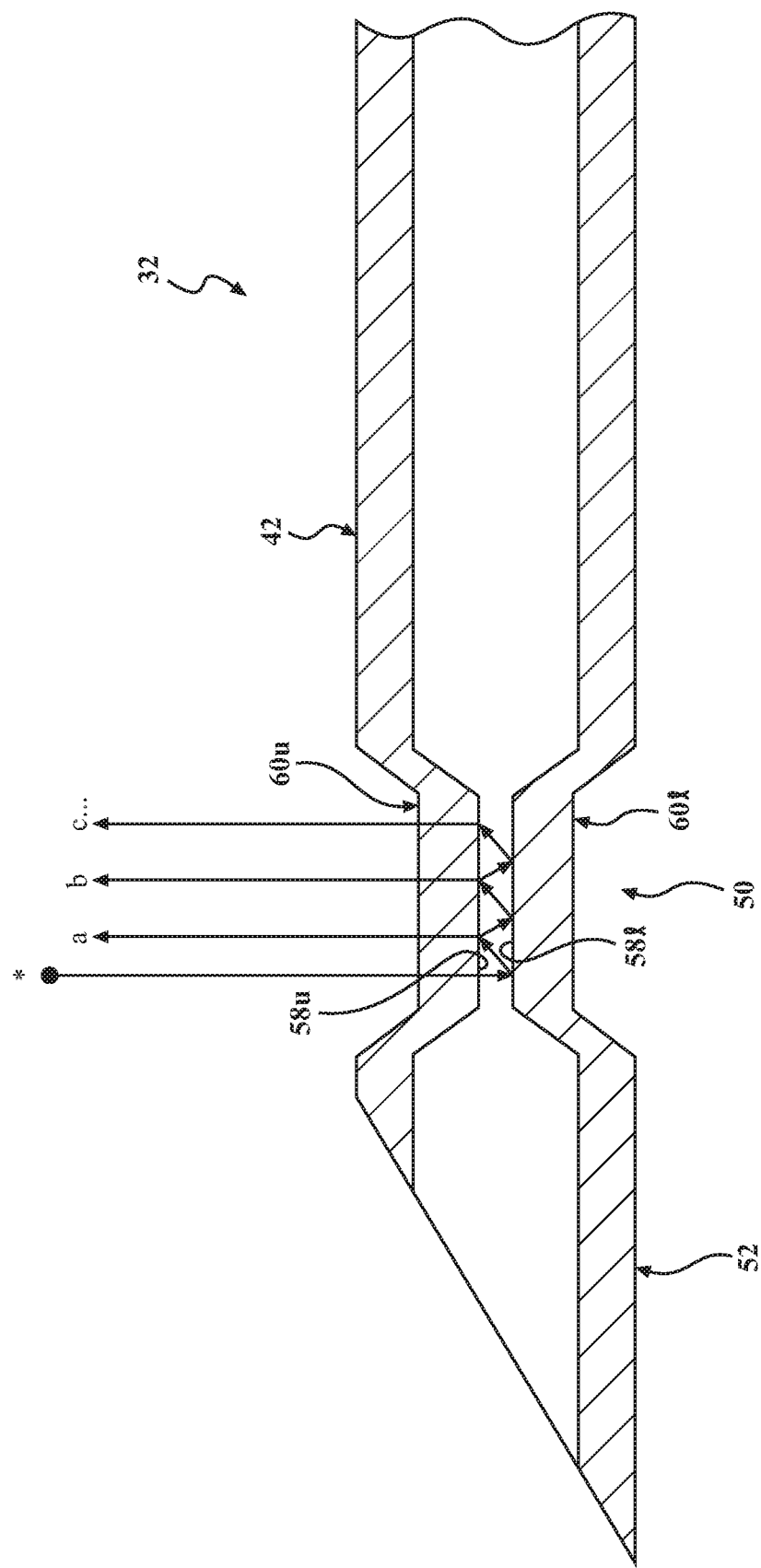
FIG. 7 is a side elevation view of the needle assembly of FIG. 3 with a schematic representation of an incident wave and reflected waves generated by a reverberation feature.
Figure 8:
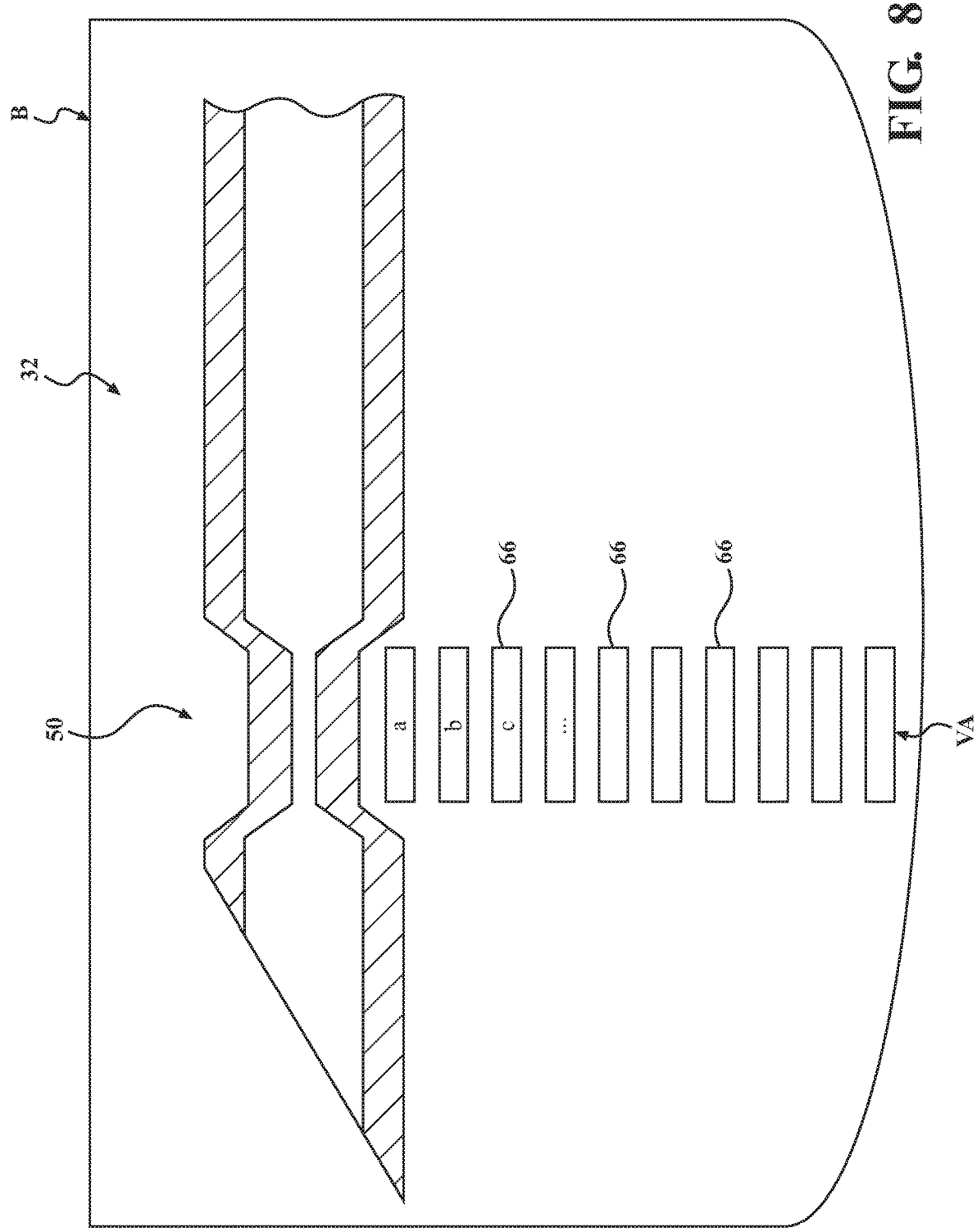
FIG. 8 a side elevation view of the needle assembly of FIG. 3 with a schematic representation of a visual artifact generated by the ultrasound system based on the reflected waves of FIG. 7.

Once the incident wave encounters the reverberation feature 50, and in particular the upper and lower portions 58u, 58l, the waves reverberate between the opposing portions 58. It is noted that for clarity FIG. 7 shows the reflected waves travelling to the right, yet in reality the incident wave(s) and reflected waves may reverberate in the same axial location. In response to the ultrasound device receiving the reflect waves, with the ultrasound system configured to generate a visual artifact (VA). In particular, the reverberated waves are received by the ultrasound system as echoes with the echoes being reproduced on the display as the visual artifact (VA), for example, a series of bright pixels 66. The visual artifact (VA) may have the appearance of a straight vertical line that begins at the reverberation feature 50 and continuing down the image, as shown in FIGS. 9 and 10, oftentimes seemingly indefinitely (but possibly decaying in brightness). The visual artifact (VA) may be referred to as a ring-down artifact. FIG. 10 shows an axial view of the visual artifact (VA) extending downwardly from the reverberation feature 50 of the needle assembly 30 through the vein (V) adjacent the artery (A). The visual artifact (VA) is distinguishable over known needle assemblies merely purporting to increase reflectivity of the needle body itself. Rather, the needle assembly 30 of the present disclosure utilizes a unique reverberation phenomenon associated with ultrasound technology. It is further noted that, owing to the curvature of a uniform smooth tubular lumen of known needle assemblies, any reflected waves are dispersed or scattered in a multi-directional manner and incapable of resulting in the visual artifact (VA) of the needle assembly 30 of the present disclosure.

The in-plane technique results in the elevation view of FIG. 9 showing the reverberation feature 50 of the needle assembly 30 positioned superior the artery (A) and the vein (V) is located. Often, discerning whether the vessel is an artery (A) or a vein (V) from the long-axis view using the in-plane technique is often difficult with the anatomical structures appearing as black and tubular in form. The short-axis view of FIG. 10 from the out-of-plane technique is used concurrently for differentiating the artery (A) and the vein (V) based on the relative collapsibility and thickness of the structures. Based on the proximity between the reverberation feature 50 and the distal tip 36, and the continuous imaging provided by a display 26 of the ultrasound system 24 (see FIG. 20), visual guidance is provided to the treating medical professional as she or he locates the distal end 36 of the needle assembly 30 at the target anatomy, for example within the vein (V). (It is noted that the needle assembly 30 would not appear as prominent as shown in FIG. 9, but rather the treating medical professional may rely almost exclusively on the visual artifact (VA) provided by the reverberation feature 50, thereby facilitating improved placement of the distal end 36 of the needle assembly 30.)

Referring now to FIGS. 11-15, the needle assembly 130 in accordance with another exemplary embodiment is shown. In at least some respects, the needle assembly 130 of the present embodiment is the same or similar to that of FIGS. 3-10 with like numerals indicating like components plus one hundred (100). Any abbreviated or omitted description of a like-numbered component is in the interest of brevity and should not be considered absent from the present embodiment. The needle assembly 130 includes an elongate body 132, and in certain embodiments an overlying sheath 134. The elongate body 132 include a distal end 136 and a proximal end (not shown) opposite the distal end 136 and extending distally from a hub (not shown). The elongate body 132 includes at least one sidewall 142 including an outer surface 144, and an inner surface 146 opposite the outer surface 144. The inner surface 146 defines a lumen 148 of the elongate body 132. The outer surface 144 may be associated with an outer diameter and the inner surface 146 associated with an inner diameter such that the elongate body 132 is substantially tubular in shape (other than a reverberation feature 150 to be described). A beveled tip 152 may define the distal end 136 of the elongate body 132 and include a point 154 defining an inferior aspect of the elongate body 132, and a heel 156 defining a superior aspect of the elongate body 132.

Figure 11:
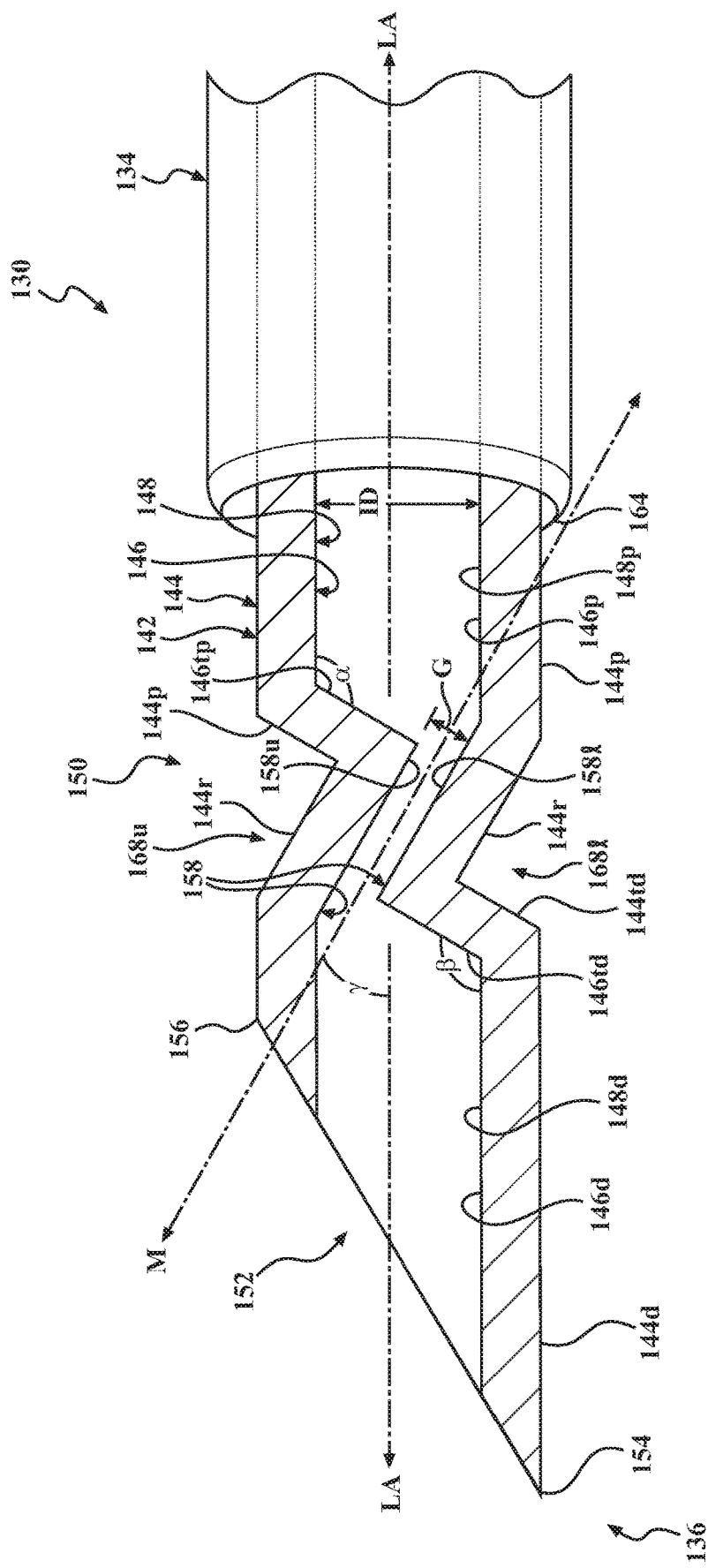
FIG. 11 is a side elevation view of a distal portion of a needle assembly in accordance with another exemplary embodiment of the present disclosure. An elongate body of the needle assembly is shown in section.

The elongate body 132 of the needle assembly 130 includes the reverberation feature 150 disposed between the distal end 136 and the proximal end. The reverberation feature 150 may include opposing portions 158 of the inner surface 146 of the sidewall 142 defining a gap (G) shaped differently than the inner surface 146 and/or sized smaller than the inner diameter (ID) of the lumen 148. The lumen 148 extending through the elongate body 132 may be defined by at least two portions, including a proximal lumen portion 148p defined by a proximal inner surface portion 146p and a distal lumen portion 148d defined by a distal inner surface portion 146p, as shown in FIG. 11. The gap (G) defined between the opposing portions 158 may axially separate and be in fluid communication with the proximal and distal lumen portions 148p, 148d.

With continued reference to FIG. 11, the inner surface 146 includes the proximal inner surface portion 146p defining the proximal lumen portion 148p that is tubular in shape. The inner surface 146 may further include at least one proximal transition inner surface portion 146tp extending inwardly or towards the longitudinal axis (LA) relative to the proximal inner surface portion 146p. Whereas the previously described embodiment of the needle assembly 30 included a proximal transition inner surface portion 46tp associated with each of the superior and inferior aspects of the elongate body 32, the present embodiment may include a single proximal transition inner surface portion 146tp. The illustrated embodiment shows the proximal transition inner surface portion 146tp associated with superior aspect of the elongate body 32; however, alternatively the proximal transition inner surface portion 146tp may be associated with the inferior aspect of the elongate body 132 (i.e., the reverberation feature 150 is "flipped"). FIG. 11 shows the proximal transition inner surface portion 146tp defining an obtuse angle, α, relative to the proximal inner surface portion 146p. The angle α may be between 95 and 175 degrees, and more particularly between 100 and 150 degrees, and even more particularly between 105 and 125 degrees.

One of the opposing portions 158 may extend distally from the proximal transition inner surface portion 146tp, and another one of the opposing portions 158 may extend distally from the proximal inner surface portion 146p. In particular, the opposing portions 158 of the reverberation feature 150 may include an upper portion 158u at the superior aspect and extending distally from the proximal transition inner surface portion 146tp, and a lower portion 158l at the inferior aspect and extending distally from the proximal inner surface portion 146p. The opposing portions 158 may be opposing planar surfaces oriented parallel to one another to define the gap (G). The arrangement results in the gap (G) being rectangular in section when viewed along a midline (M) between the opposing portions 158, and thus shaped differently than the lumen 148 being cylindrical in axial section. In the illustrated embodiment, the opposing planar surfaces are further oriented at an angle relative to the longitudinal axis (LA). In particular, the opposing planar surfaces are oriented angularly upward in a proximal-to-distal direction such that the midline (M) between the opposing planar surfaces and the longitudinal axis (LA) define an acute angle, γ, as shown in FIG. 11. The angle γ may be between 5 and 75 degrees, and more particularly between 10 and 60 degrees, and even more particularly between 15 and 45 degrees. The angle γ may correspond to a preferred angle of approach θ of the needle assembly 30 to be directed into the patient anatomy such that the opposing portions 158 are substantially perpendicular to the incident wave(s) being directed from the ultrasound device 23, as to be further described with respect to FIG. 14. In one example of venipuncture for blood sampling, it is often desirable for the angle of approach θ to be approximately thirty degrees, and thus the angle γ may also be approximately thirty degrees such that the opposing portions 158 are substantially horizontal relative to or parallel to the overlying skin surface of the patient against which the ultrasound device 23 may be positioned.

Figure 13:
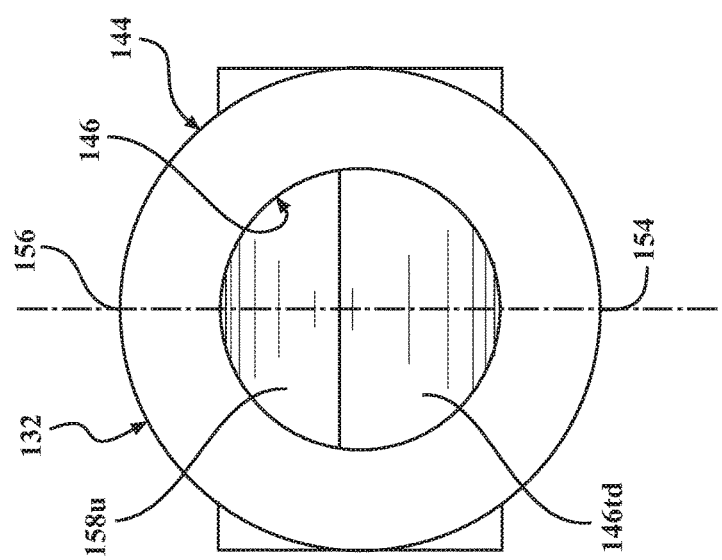
FIG. 13 is an axial view of the needle assembly of FIG. 11.
Figure 12:
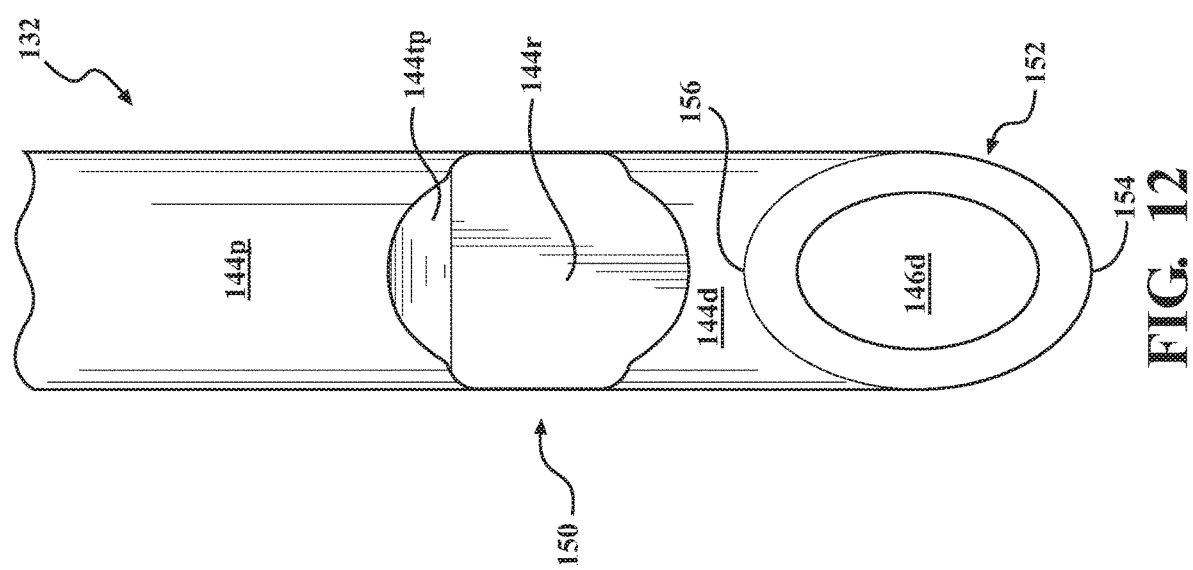
FIG. 12 is a top plan view of the needle assembly of FIG. 11.

Extending distally from one of the opposing portions 158 may be a distal transition inner surface portion 146td (also shown in the axial view of FIG. 13). Whereas the previously described embodiment of the needle assembly 30 included a distal transition inner surface portion 46td associated with both of the opposing portions 58, the present embodiment may include a single distal transition inner surface portion 146td. The illustrated embodiment shows the proximal transition inner surface portion 146tp associated with the lower portion 158l of the reverberation feature 150; however, alternatively the distal transition inner surface portion 146td may be associated with the inferior aspect of the elongate body 132 (i.e., the reverberation feature 150 is "flipped"). The distal transition inner surface portion 146td extends outwardly or away from the longitudinal axis (LA) of the elongate body 132. The distal transition inner surface portions 146td may be equal in length to the proximal transition inner surface portion 146tp such that the inner diameter of the distal and proximal lumen portions 148p, 148d are equal. The distal inner surface portion 146d may extend distally from the distal transition inner surface portion 146td as well as the upper portion 158u of the reverberation feature 150. FIG. 11 shows the distal inner surface portion 146d defining an obtuse angle, β, relative to the distal transition inner surface portion 146td. The angle θ may be between 95 and 175 degrees, and more particularly between 100 and 150 degrees, and even more particularly between 105 and 125 degrees. The angle θ may be equal to the angle α. The distal inner surface portion 146d may defined at least a portion of the beveled tip 152.

The outer surface 144 may be contoured to the inner surface 146 to define the sidewall 142 of substantially constant thickness. The illustrated embodiment of FIG. 11 shows the outer surface 144 including a proximal portion 144p, a proximal transition portion 144tp, reverberation portions 144r corresponding to the opposing portions 158, a distal transition portion 144td, and a distal portion 144d. The outer surface 144 being contoured to the inner surface 146 may result in one or more notches 168, more specifically an upper notch 168u and a lower notch 168l. The upper notch 168u may be defined between the upper portion 158u of the inner surface 146 and one of the reverberation portions 144r of the outer surface 144, and the lower notch 168l may be defined between the lower portion 158l of the inner surface 146 and the other one of the reverberation portions 144r of the outer surface 144. The illustrated embodiment shows the notches 168 being generally V-shaped when viewed in elevation. The lower notch 168l may be complementary to the upper notch 168u, and more particularly complimentarily shaped in a manner to be axially spaced apart from the upper notch 168u along the longitudinal axis (LA) to define the gap (G). The top plan view of FIG. 5 shows the contour of the outer surface 144 including the upper notch 168u.

The reverberation feature 150 may be positioned at or near the distal end 136 of the elongate body 132, for example, immediately proximal to the beveled tip 152. Further, in embodiments including an overlying sheath 134, the sheath 134 may include a distal end 164 axially positioned proximal to the reverberation feature 150.

Figure 14:
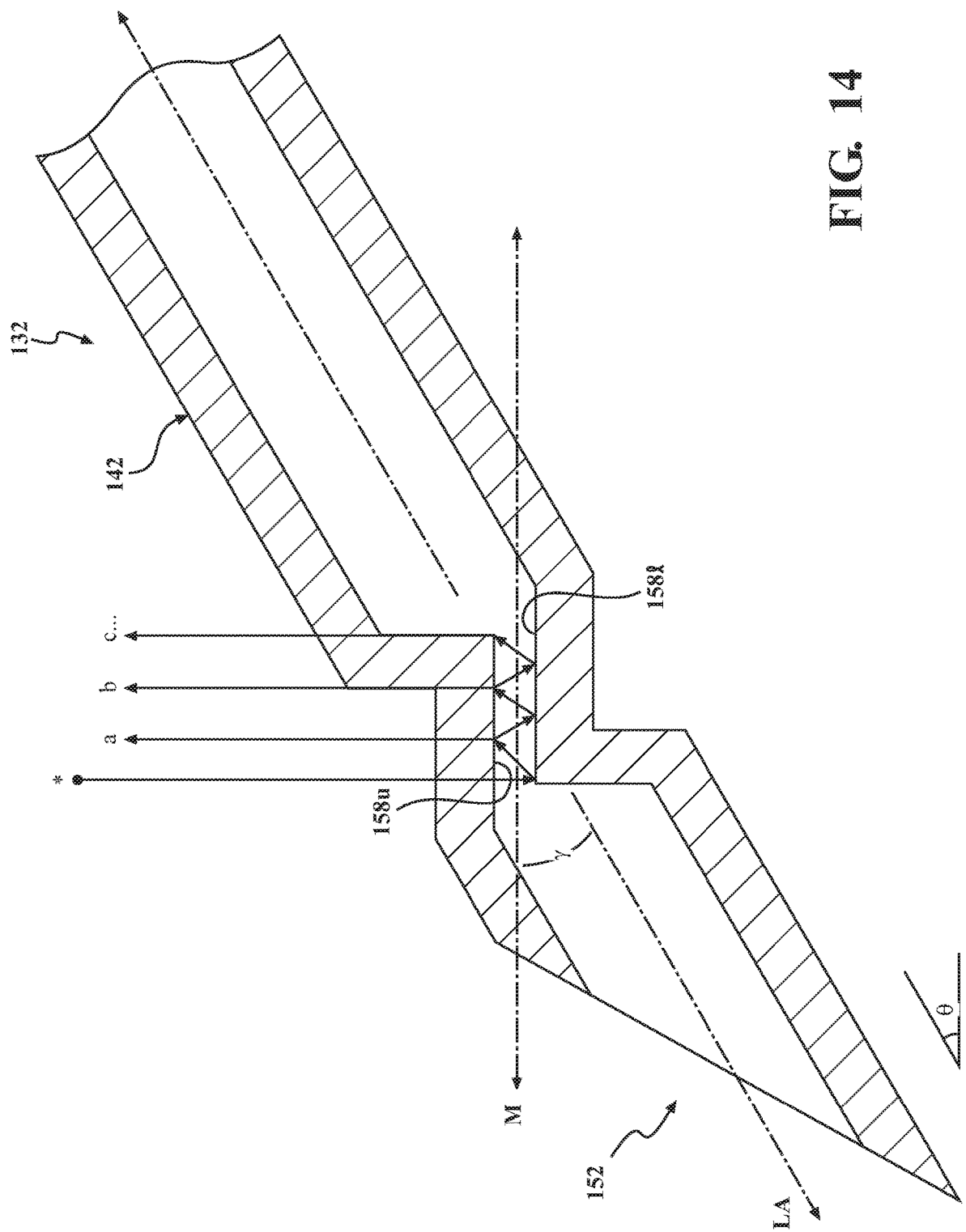
FIG. 14 is a side elevation view of the needle assembly of FIG. 11 positioned at an angle of approach with a schematic representation of an incident wave and reflected waves generated by a reverberation feature.
Figure 15:
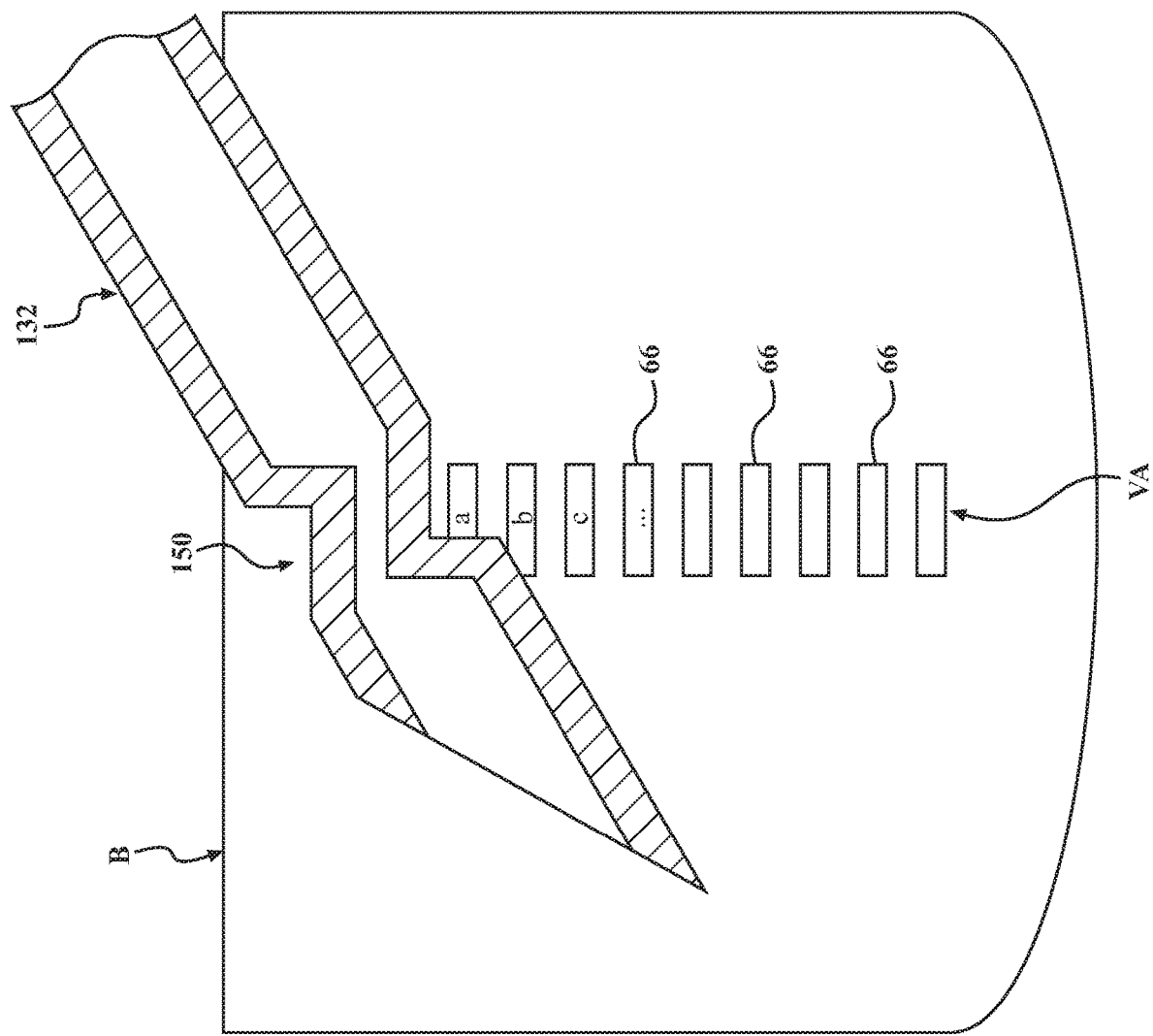
FIG. 15 a side elevation view of the needle assembly of FIG. 13 positioned at the angle of approach of FIG. 14 with a schematic representation of a visual artifact generated by the ultrasound system.

Operation of the reverberation feature 150 will now be described with reference to FIGS. 14 and 15. With the needle assembly 130 is percutaneously advanced and positioned near the target anatomy, for example a vein (V) (see FIGS. 9 and 10). The elongate body 132 may be directed toward and/or positioned within the patient anatomy at the angle of approach θ relative to horizontal or, for example, the overlying tissue of the patient. The angle of approach θ may be any suitable angle but generally is within the range of five to forty-five degrees. In certain embodiments, the angle of approach θ is substantially equal to the angle γ such that the opposing portions 158 are substantially perpendicular to the incident wave (*). Because the opposing portions 158 are substantially perpendicular to the incident wave (*) at the angle of approach θ, the treating medical professional need not significantly orient the ultrasound device 23 relative to the overlying tissue of the patient to produce a visual artifact (VA) to be described. The ultrasound device 23 is operated to direct the incident wave(s) (*) through the target anatomy and the needle assembly 130 positioned therein, and once the incident wave(s) (*) encounter the reverberation feature 150, and in particular the upper and lower portions 158u, 158l, the waves reverberate between the opposing portions 158. In response to the ultrasound device 23 receiving the reflect waves, with the ultrasound system 24 configured to generate the visual artifact (VA). In particular, the reverberated waves are received by the ultrasound system as echoes with the echoes being reproduced on the display 26 as the visual artifact (VA). Based on the proximity between the reverberation feature 150 and the distal tip 136, and the continuous imaging provided by the ultrasound system 24, visual guidance is provided to the treating medical professional as she or he locates the distal end 136 of the needle assembly 130 at the target anatomy.

Referring now to FIGS. 16-19C, a needle assembly 230 in accordance with another exemplary embodiment is shown. In at least some respects, the needle assembly 230 of the present embodiment is the same or similar to that of FIGS. 3-15 with like numerals indicating like components plus multiples of one hundred (100). Any abbreviated or omitted description of a like-numerated component is in the interest of brevity and should not be considered absent from the present embodiment. The needle assembly 230 includes an elongate body 232, and in certain embodiments an overlying sheath 234. The elongate body 232 includes a distal end 236 and a proximal end (not shown) opposite the distal end 236 and extending distally from a hub (not shown). The elongate body 232 includes at least one sidewall 242 including an outer surface 244, and an inner surface 246 opposite the outer surface 244. The inner surface 246 defines a lumen 248 of the elongate body 232. The outer surface 244 may be associated with an outer diameter and the inner surface 246 associated with an inner diameter such that the elongate body 232 is substantially tubular in shape (other than a reverberation feature 250 to be described). A beveled tip 252 may define the distal end 236 of the elongate body 232 and include a point 254 defining an inferior aspect of the elongate body 232, and a heel 256 defining a superior aspect of the elongate body 232.

Figure 16:
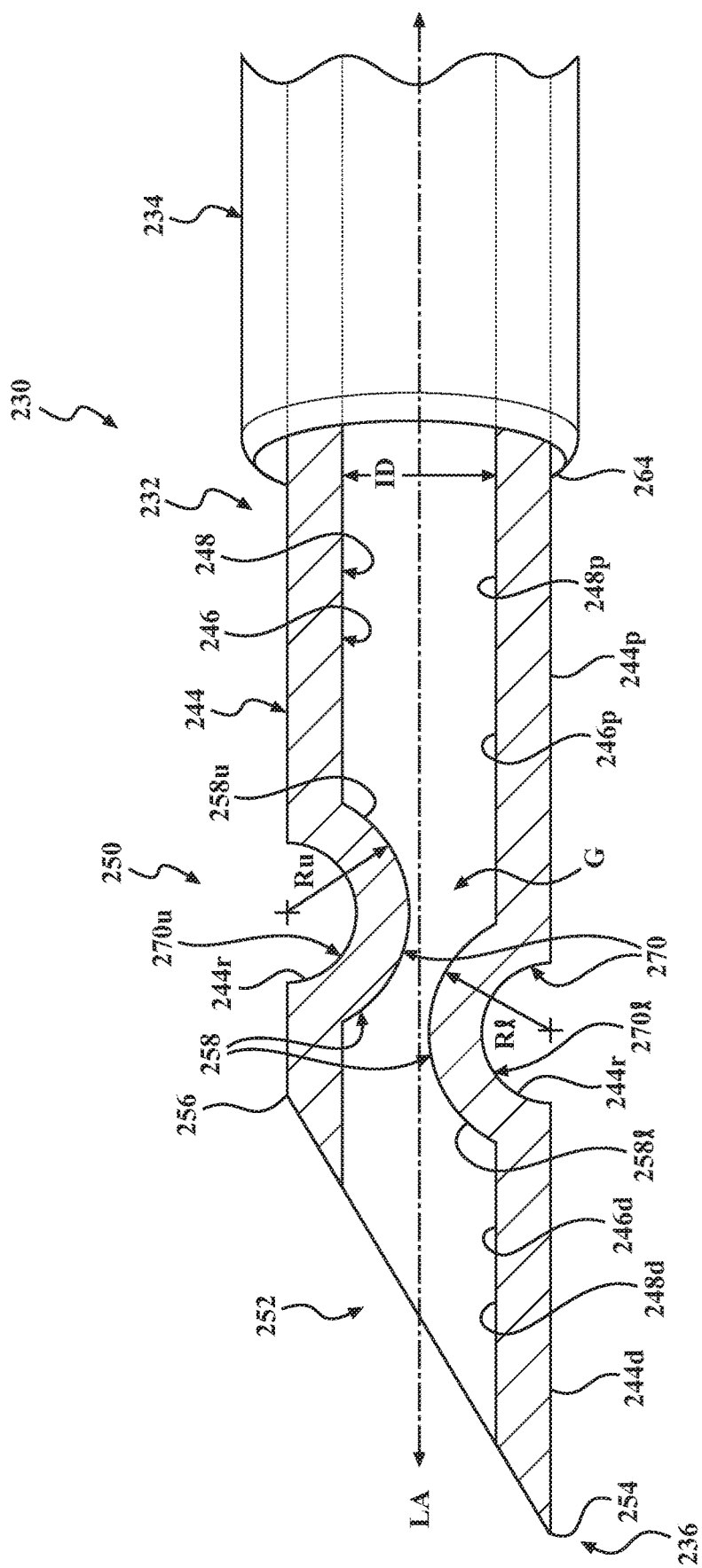
FIG. 16 is a side elevation view of a distal portion of a needle assembly in accordance with another exemplary embodiment of the present disclosure. An elongate body of the needle assembly is shown in section.
Figure 18:
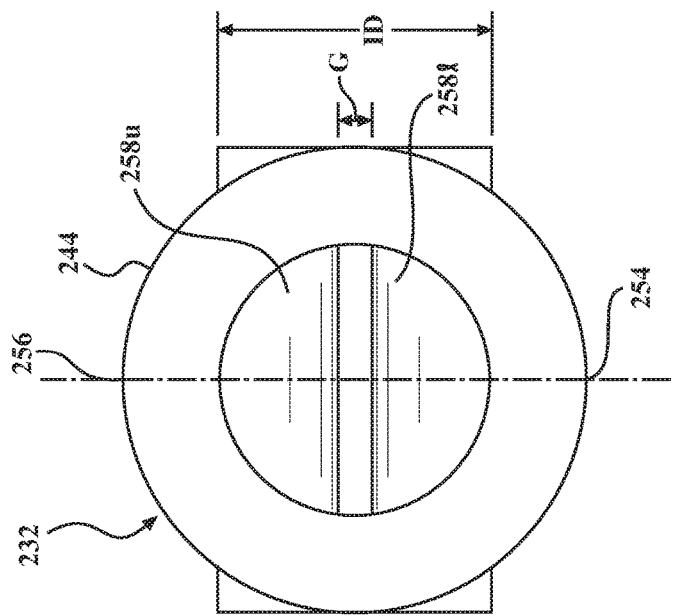
FIG. 18 is an axial view of the needle assembly of FIG. 16.

The elongate body 232 of the needle assembly 230 includes the reverberation feature 250 disposed between the distal end 236 and the proximal end. The reverberation feature 250 may include opposing portions 258 of the inner surface 246 of the sidewall 242 defining a gap (G) shaped differently than the inner surface 246 and/or sized smaller than the inner diameter (ID) of the lumen 248. The lumen 248 extending through the elongate body 232 may be defined by at least two portions, including a proximal lumen portion 248p defined by a proximal inner surface portion 246p and a distal lumen portion 248d defined by a distal inner surface portion 246p, as shown in FIG. 16. The gap (G) defined between the opposing portions 258 may axially separate and be in fluid communication with the proximal and distal lumen portions 248p, 248d.

With continued reference to FIG. 16, the inner surface 246 includes the proximal inner surface portion 246p defining the proximal lumen portion 248p that is tubular in shape. The opposing portions 258 may extend distally from the proximal inner surface portion 246p and extending inwardly or towards the longitudinal axis (LA) relative to the proximal inner surface portion 246p. In particular, the opposing portions 258 of the reverberation feature 250 may include an upper portion 258u at the superior aspect and a lower portion 258l at the inferior aspect. The opposing portions 258 may be arcuate surfaces extending towards the longitudinal axis (LA) to define the gap (G). The arrangement results in the gap (G) being variable in size, and thus shaped differently than the lumen 248 being cylindrical in axial section. In the illustrated embodiment, the opposing arcuate surfaces are semicircular in shape and positioned to at least partially overlap axially along the longitudinal axis (LA). The upper portion 258u may include a radius of curvature $R_u$ of between 0.001 and five millimeters, and the lower portion 258l may include a radius of curvature $R_l$ of between 0.001 and five millimeters. The radii of curvature $R_u$, $R_l$ of the upper and lower portions 258u, 258l may be equal, and further may vary based on the dimensions of the elongate body 232 (e.g., the gauge of the needle assembly 230). Extending distally from the opposing portions 258 may be a distal inner surface portion 246d. The distal inner surface portion 246d may define at least a portion of the beveled tip 252.

Figure 17:
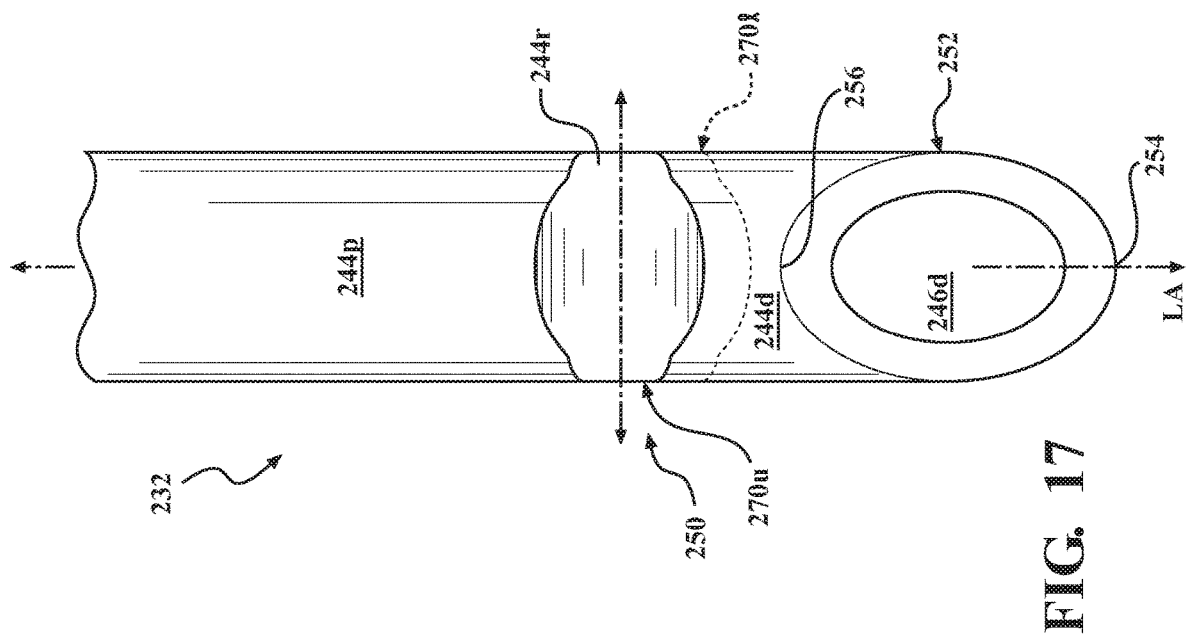
FIG. 17 is a top plan view of the needle assembly of FIG. 16.

The outer surface 244 may be contoured to the inner surface 246 to define the sidewall 242 of substantially constant thickness. The illustrated embodiment of FIG. 16 shows the outer surface 244 including a proximal portion 244p, reverberation portions 244r corresponding to the opposing portions 258, and a distal portion 244d. The outer surface 244 being contoured to the inner surface 246 may result in one or more arcuate protrusions 270, more specifically an upper arcuate protrusion 270u and a lower arcuate protrusion 270l. The upper arcuate protrusion 270u may be defined between the upper portion 258u of the inner surface 246 and one of the reverberation portions 244r of the outer surface 244, and the lower arcuate protrusion 270l may be defined between the lower portion 258l of the inner surface 246 and the other one of the reverberation portions 244r of the outer surface 244. The illustrated embodiment shows the arcuate protrusions 270 being hemicylindrical in shape and oriented transverse (TR) to the longitudinal axis (LA), as shown in FIG. 17. The lower arcuate protrusion 270l may be complementary to the upper arcuate protrusion 270u, and more particularly complimentarily shaped in a manner to be axially spaced apart from the upper arcuate protrusion 270u along the longitudinal axis (LA) to define the gap (G). The top plan view of FIG. 17 shows the contour of the outer surface 244 including the upper arcuate protrusion 270u.

The reverberation feature 250 may be positioned at or near the distal end 236 of the elongate body 232, for example, immediately proximal to the beveled tip 252. Further, in embodiments including an overlying sheath 234, the sheath 234 may include a distal end 264 axially positioned proximal to the reverberation feature 250.

Figure 19A:
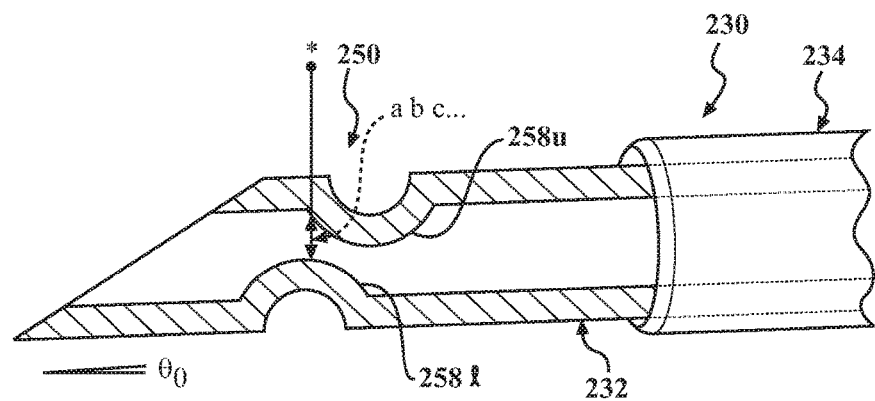
FIG. 19A is a side elevation view of the needle assembly of FIG. 16 positioned at a first angle of approach with a schematic representation of an incident wave and reflected waves generated by a reverberation feature.

Among other advantages, the needle assembly 230 of the present embodiment allows for opposing points on the opposing arcuate surfaces 258 to be oriented substantially perpendicular to the incident wave (*) throughout a range of angles of approach θ. Operation of the reverberation feature 250 will now be described with reference to FIGS. 19A-19C. With the needle assembly 230 is percutaneously advanced and positioned near the target anatomy, for example a vein (V) (see FIGS. 9 and 10). The elongate body 232 may be directed toward and/or positioned within the patient anatomy at a first angle of approach $\theta_0$ relative to horizontal or, for example, the overlying tissue of the patient. The first angle of approach $\theta_0$ may be relatively shallow, for example, between one and five degrees. Owing to the axial spacing and the complementary radii of curvature $R_u$, $R_l$ of the upper and lower portions 258u, 258l, a point on each of the upper arcuate surface and the lower arcuate surface is perpendicular to the incident wave(s) (*) (and the reflected wave(s) (a, b, c, . . . )), as shown in FIG. 19A. The ultrasound device 22 is operated to direct the incident wave(s) (*) through the target anatomy and the needle assembly 230 positioned therein, and the waves reverberate between the opposing portions 258. In response to the ultrasound device receiving the reflected waves, with the ultrasound system configured to generate a visual artifact (VA). Based on the proximity between the reverberation feature 250 and the distal tip 236, and the continuous imaging provided by the ultrasound system 24, visual guidance is provided to the treating medical professional as she or he locates the distal end 216 of the needle assembly 230 at the target anatomy.

Figure 19B:
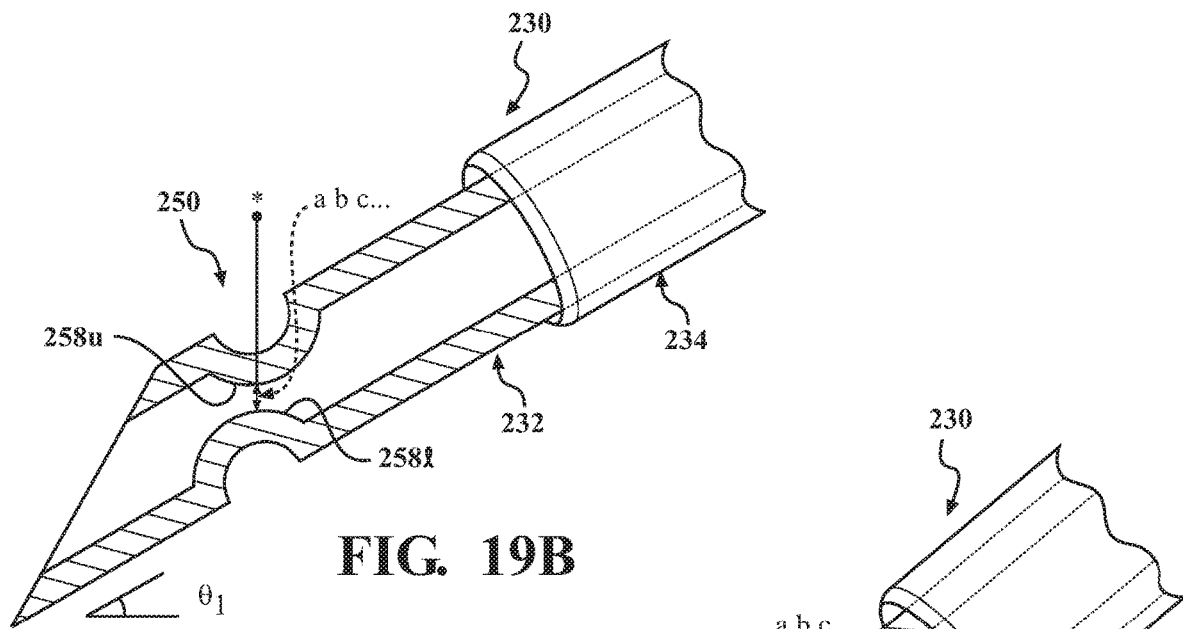
FIG. 19B is a side elevation view of the needle assembly of FIG. 16 positioned at a second angle of approach with a schematic representation of an incident wave and reflected waves generated by a reverberation feature.

The elongate body 232 may be directed toward, positioned, and/or repositioned within the patient anatomy at a second angle of approach $\theta_1$ relative to horizontal or, for example, the overlying tissue of the patient. The second angle of approach $\theta_1$ may be greater than (i.e., steeper) the first angle of approach $\theta_0$. Owing to the axial spacing and the complementary radii of curvature $R_u$, $R_l$ of the upper and lower portions 258u, 258l, a point on each of the upper arcuate surface and the lower arcuate surface is perpendicular to the incident wave(s) (*) (and the reflected wave(s) (a, b, c, . . . )), as shown in FIG. 19B, without needing to adjust the ultrasound device 23 positioned above the overlying tissue. Likewise, the elongate body 232 may be directed toward, positioned, and/or repositioned within the patient anatomy at a third angle of approach $\theta_2$ relative to horizontal or, for example, the overlying tissue of the patient. The third angle of approach $\theta_2$ may be greater than (i.e., steeper) the first and second angles of approach $\theta_0$, $\theta_1$. Again, owing to the axial spacing and the complementary radii of curvature $R_u$, of the upper and lower portions 258u, 258l, a point on each of the upper arcuate surface and the lower arcuate surface is perpendicular to the incident wave(s) (*) (and the reflected wave(s) (a, b, c, . . . )), as shown in FIG. 19BC without needing to adjust the ultrasound device 23 positioned above the overlying tissue. As a result, the waves reverberate between the opposing portions 258 through a range of angles of approach θ, and thus visual artifact (VA) remains displayed throughout the range of angles of approach θ without needing to adjust the ultrasound device 23. The range of angles of approach θ from which the present embodiment of the needle assembly 230 is capable of reverberating the waves may be between 1 and 85 degrees, more particularly between 5 and 75 degrees, and even more particularly between 10 and 65 degrees. Such an embodiment of the needle assembly 230 may be particularly well suited with the ultrasound device 23 coupled to the anatomy of the patient, thereby freeing one of the hands of the treating medical professional for other tasks of the medical procedure.

Figure 19C:
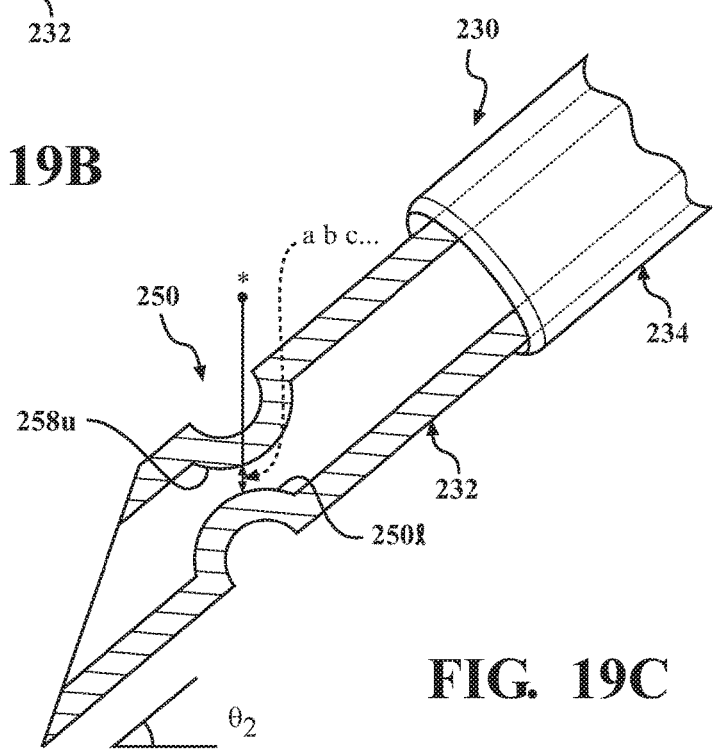
FIG. 19C is a side elevation view of the needle assembly of FIG. 16 positioned at a third angle of approach with a schematic representation of an incident wave and reflected waves generated by a reverberation feature.
Figure 20:
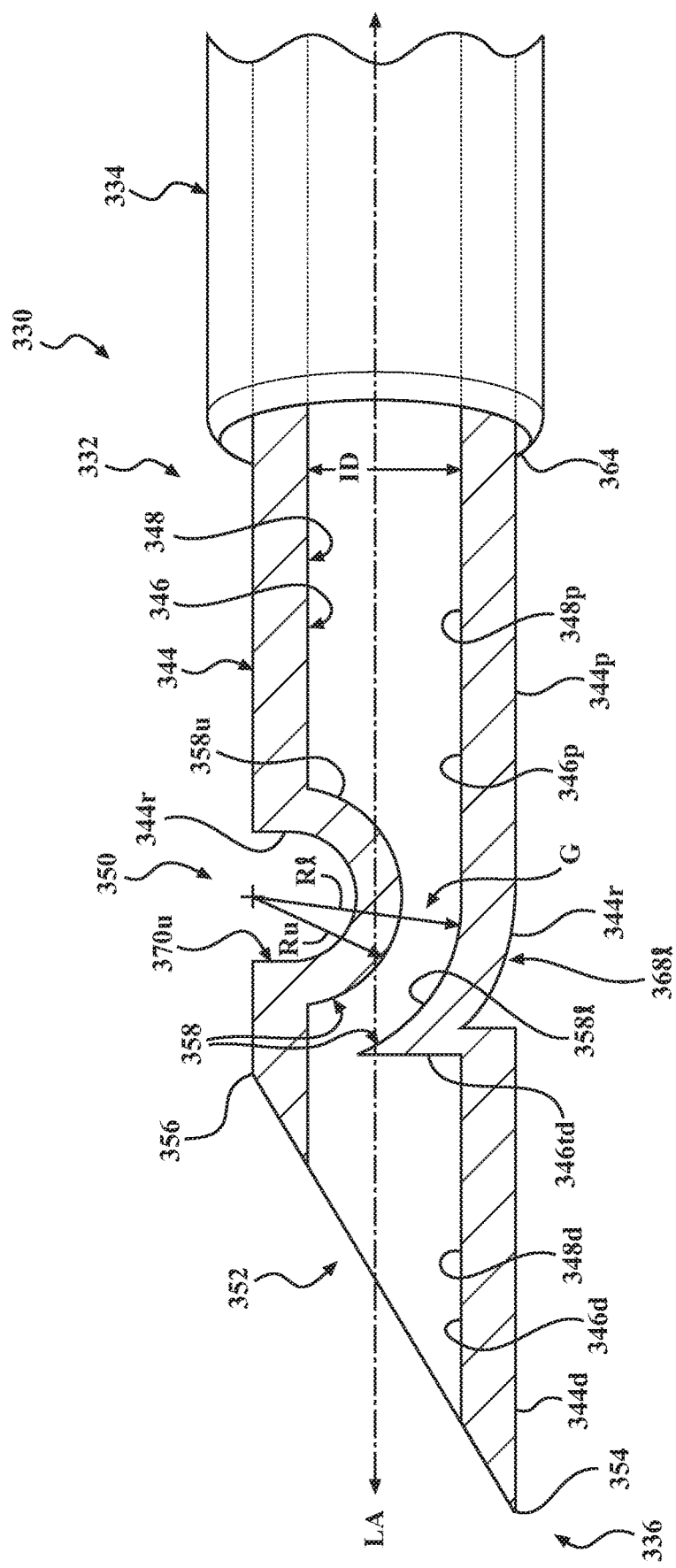
FIG. 20 is a side elevation view of a distal portion of a needle assembly in accordance with another exemplary embodiment of the present disclosure. An elongate body of the needle assembly is shown in section.

Referring now to FIGS. 20-22, a needle assembly 330 in accordance with another exemplary embodiment is shown. In at least some respects, the needle assembly 330 of the present embodiment is the same or similar to that of FIGS. 3-19C with like numerals indicating like components plus multiples of one hundred (100). Any abbreviated or omitted description of a like-numerated component is in the interest of brevity and should not be considered absent from the present embodiment. The needle assembly 330 includes an elongate body 332, and in certain embodiments an overlying sheath 334. The elongate body 332 includes a distal end 336 and a proximal end (not shown) opposite the distal end 336 and extending distally from a hub (not shown). The elongate body 332 includes at least one sidewall 342 including an outer surface 344, and an inner surface 346 opposite the outer surface 344. The inner surface 346 defines a lumen 348 of the elongate body 332. The outer surface 344 may be associated with an outer diameter and the inner surface 346 associated with an inner diameter such that the elongate body 332 is substantially tubular in shape (other than a reverberation feature 350 to be described). A beveled tip 352 may define the distal end 336 of the elongate body 332 and include a point 354 defining an inferior aspect of the elongate body 332, and a heel 356 defining a superior aspect of the elongate body 332.

The elongate body 332 of the needle assembly 330 includes the reverberation feature 350 disposed between the distal end 336 and the proximal end. The reverberation feature 350 may include opposing portions 358 of the inner surface 346 of the sidewall 342 defining a gap (G) shaped differently than the inner surface 346 and/or sized smaller than the inner diameter (ID) of the lumen 348. The lumen 348 extending through the elongate body 332 may be defined by at least two portions, including a proximal lumen portion 348*p* defined by a proximal inner surface portion 346*p* and a distal lumen portion 348*d* defined by a distal inner surface portion 346*p*, as shown in FIG. 20. The gap (G) defined between the opposing portions 358 may axially separate and be in fluid communication with the proximal and distal lumen portions 348*p*, 348*d*.

With continued reference to FIG. 20, the inner surface 346 includes the proximal inner surface portion 346*p* defining the proximal lumen portion 348*p* that is tubular in shape. The opposing portions 358 may extend distally from the proximal inner surface portion 346*p* and extending inwardly or towards the longitudinal axis (LA) relative to the proximal inner surface portion 346*p*. In particular, the opposing portions 358 of the reverberation feature 350 may include an upper portion 358*u* at the superior aspect and a lower portion 358*l* at the inferior aspect. The upper portion 358*u* may be an arcuate surface extending towards the longitudinal axis (LA) to define the gap (G). The illustrated embodiment shows the upper portion 358*u* as a semicircular surface extending through the longitudinal axis (LA). The lower portion 358*l* may also be an arcuate surface extending distally from the proximal inner surface portion 346*p*. The arcuate surface of the lower portion 358*l* may begin at approximately a midpoint of the semicircular surface defining the upper portion 358*u*. Thus, the opposing arcuate surfaces are positioned to at least partially overlap axially along the longitudinal axis (LA). The upper portion 358*u* may include a radius of curvature $R_u$ of between 0.001 and five millimeters, and the lower portion 358*l* may include a radius of curvature $R_l$ of between 0.001 and five millimeters. The radii of curvature $R_u$, $R_l$ of the upper and lower portions 358*u*, 358*l* may be equal, and further may vary based on the dimensions of the elongate body 332 (e.g., the gauge of the needle assembly 330). The arrangement results in the gap (G) being substantially constant in size between the opposing portions 358, yet the gap (G) is smaller than and shaped differently than the lumen 348 being cylindrical in axial section. It is also contemplated that the gap (G) may vary in size in the present embodiment of the needle assembly 330.

Extending distally from may be a distal inner surface portion 346*d*. Extending distally from the lower portion 358*l* may be a distal transition inner surface portion 346*td* (also shown in the axial view of FIG. 6). The distal transition inner surface portion 346*td* extends outwardly or away from the longitudinal axis (LA) of the elongate body 332 relative to a proximal-most aspect of the lower portion 358*l*. The distal inner surface portion 346*d* may extend distally from the distal transition inner surface portion 346*td* and the upper portion 358*u*. The distal inner surface portion 346*d* may define at least a portion of the beveled tip 352. In the illustrated embodiment, the distal transition inner surface portion 346*td* is a vertical surface defining a horizontal edge with the lower portion 358*l*. It is contemplated that the distal transition inner surface portion 346*td* may alternative be angled towards the distal end 336 to provide a smoother transition to the lower portion 358*l*, and/or extend upwardly near the superior aspect of the elongate body 332. In certain embodiments, particularly those with the overlying sheath 334, the distal transition inner surface portion 346*td* may extend superiorly to create a distal portion of the elongate body 332 may be solid in axial section.

The outer surface 344 may be contoured to the inner surface 346 to define the sidewall 342 of substantially constant thickness. The illustrated embodiment of FIG. 20 shows the outer surface 344 including a proximal portion 344*p*, reverberation portions 344*r* corresponding to the opposing portions 358, and a distal portion 344*d*. The outer surface 344 being contoured to the inner surface 346 may result in an upper arcuate protrusion 370*u* and a lower notch 268*l*. The upper arcuate protrusion 370*u* may be defined between the upper portion 358*u* of the inner surface 346 and one of the reverberation portions 344*r* of the outer surface 344. The lower notch 368*l* may be defined between the lower portion 358*l* of the inner surface 346 and the other one of the reverberation portions 344*r* of the outer surface 344. The illustrated embodiment shows the upper arcuate protrusions 370*u* being hemicylindrical in shape and oriented transverse (TR) to the longitudinal axis (LA), as shown in FIG. 21. The lower notch 368*l* may be complementary to the upper arcuate protrusion 370*u*, and more particularly complimentarily shaped in a manner to be axially spaced apart from the upper arcuate protrusion 370u along the longitudinal axis (LA) to define the gap (G). The top plan view of FIG. 21 shows the contour of the outer surface 344 including the upper arcuate protrusion 370u and the lower notch 368l including the distal transition inner surface portion 346td in phantom.

The reverberation feature 350 may be positioned at or near the distal end 336 of the elongate body 332, for example, immediately proximal to the beveled tip 252. Further, in embodiments including an overlying sheath 334, the sheath 334 may include a distal end 364 axially positioned proximal to the reverberation feature 350.

Among other advantages, the needle assembly 330 of the present embodiment allows for opposing points on the opposing arcuate surfaces 358 to be oriented substantially perpendicular to the incident wave (*) throughout a range of angles of approach θ, in a manner of operation similar to the previously embodiment of the needle assembly 230 described with reference to FIGS. 19A-19C. In particular, owing to the axial spacing and the complementary radii of curvature $R_u$, $R_l$ of the upper and lower portions 358u, 358l, a point on each of the upper arcuate surface and the lower arcuate surface is perpendicular to the incident wave(s) (*) (and the reflected wave(s) (a, b, c, ... )), through a range of angles of approach θ. As a result, the waves reverberate between the opposing portions 358 through the range of angles of approach θ, and visual artifact (VA) remains displayed throughout the range of angles of approach θ without needing to adjust the ultrasound device 23. The range of angles of approach θ from which the present embodiment of the needle assembly 330 is capable of reverberating the waves may be between 1 and 85 degrees, more particularly between 5 and 75 degrees, and even more particularly between 10 and 65 degrees. Such an embodiment of the needle assembly 330 may be particularly well suited with the ultrasound device 23 coupled to the anatomy of the patient, thereby freeing one of the hands of the treating medical professional for other tasks of the medical procedure.

Figure 23:
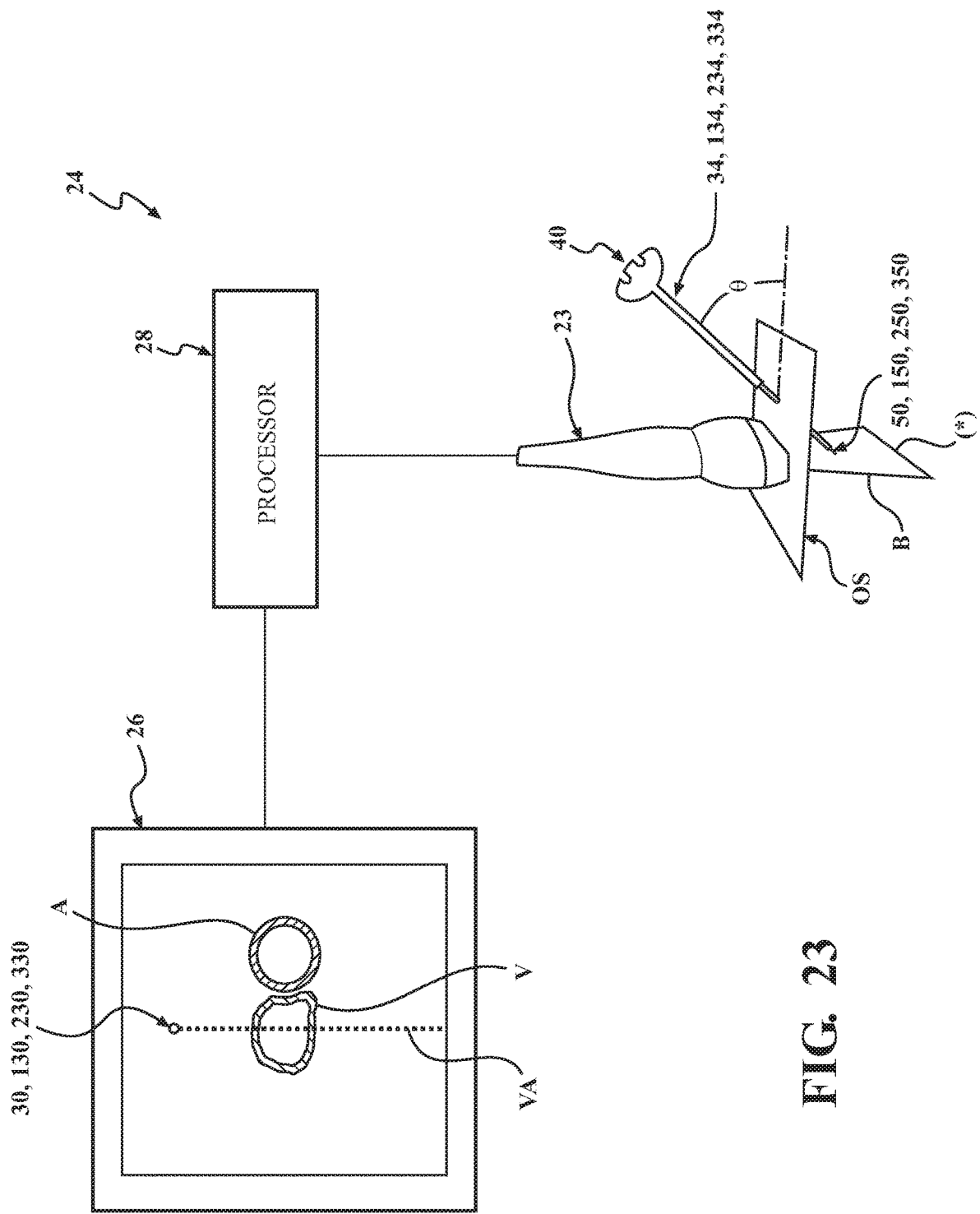
FIG. 23 is a schematic diagram of an ultrasound system for facilitating visual guidance with the needle assemblies of the present disclosure.

Referring now to FIG. 23, a method of positioning the needle assembly 30, 130, 230, 330 within a target anatomy of a patient under visual guidance from an ultrasound system 24 is described. The ultrasound system 24 includes the ultrasound device 22, for example a probe 23 capable of being manipulated by the treating medical professional. The ultrasound system 24 also includes a display 26 in electronic communication with the probe 23. A processor 28 may be in electronic communication with the probe 23 and the display 26 and configured to receive and process signals from the probe 23 and transmit display signals to the display 26.

The needle assembly 30, 130, 230, 330 may be any one of the aforementioned embodiments. The needle assembly 30, 130, 230, 330 includes the elongate body 32, 132, 232, 332 the beveled tip 52, 152, 252, 352 the sidewall 42, 142, 242, 342 defining the lumen 48, 148, 248, 348 and the reverberation feature 50, 150, 250, 350. The reverberation feature 50, 150, 250, 350 includes the opposing portions 58, 158, 258, 358 of the inner surface 46, 146, 246, 346 defining the gap (G) shaped differently than the inner surface 46, 146, 246, 346, for example, smaller than the inner diameter defined by the lumen 48, 148, 248, 348. The beveled tip 52, 152, 252, 352 is penetrated through the overlying skin surface (OS) to direct the needle assembly 30, 130, 230, 330 towards the target anatomy, for example a vessel such as a vein (V) or artery (A). The needle assembly 30, 130, 230, 330 is directed towards the target anatomy at an angle of approach θ relative to the overlying skin surface (OS). The probe 23 is positioned external to the overlying skin surface (OS) at a location above the target anatomy. The probe 23 is operated to direct an incident wave (*) (see FIGS. 7, 14 and 19A-19C) through the overlying skin surface (OS) and towards the target anatomy. The needle assembly 30, 130, 230, 330 and/or the probe 23 is manipulated such that the incident wave is reverberated with the reverberation feature 50, 150, 250, 350 to generate reflected waves (a, b, c, ... (see FIGS. 7, 14 and 19A-19C)). For example, the needle assembly 30, 130, 230, 330 and/or the probe 23 may be manipulated to substantially align the opposing portions 58, 158, 258 of the reverberation feature 50, 150, 250, 350 with the incident wave (*). Further, the needle assembly 30, 130, 230, 330 and/or the probe 23 may be manipulated to alter the angle of approach θ of the needle assembly such that the opposing portions 58, 158, 258, 358 of the reverberation feature 50, 150, 250, 350 are oriented substantially perpendicular to the incident wave (*) directed from the probe 23. Still further, in embodiments where the opposing portions 258, 358 of the needle assembly 230, 330 includes the opposing arcuate surfaces, the needle assembly 230, 330 may be manipulated through a range of angles of approach θ. Opposing points on the opposing arcuate surfaces are oriented substantially perpendicular to the incident wave (*) directed from the probe throughout the range of angles of approach θ.

The method may include viewing on the display 26 the visual artifact (VA) generated with the ultrasound system 24 based on the reflected waves (a, b, c, ... ). The needle assembly 30, 130, 230, 330 and/or the probe 23 may be manipulated to cause the visual artifact (VA) to intersect a cross section of the vessel, for example the vein (V), as shown in FIG. 20.

In embodiments where the needle assembly 30, 130, 230, 330 further includes the overlying sheath 34, 134, 234, 334, the needle assembly 30, 130, 230, 330 may be manipulated to cause the beveled tip 52, 152, 252, 352 and a distal end 64, 164, 264, 364 of the overlying sheath 34, 134, 234, 334 to penetrate the vessel. The distal end 64, 164, 264, 364 of the overlying sheath 34, 134, 234, 334 may be proximal to the reverberation feature 50, 150, 250, 350 of the elongate body 32, 132, 232, 332. Based on the visual artifact (VA) displayed on the display 26 and generated by the reverberation feature 50, 150, 250, 350 reverberating the waves, placement of the needle assembly 30, 130, 230, 330 (including the distal end 64, 164, 264, 364 of the overlying sheath 34, 134, 234, 334) may be confirmed. Thereafter, the elongate body 32, 132, 232, 332 of the needle assembly 30, 130, 230, 330 may be removed from within the vessel and the overlying sheath 34, 134, 234, 334 while leaving the distal end 64, 164, 264, 364 of the overlying sheath 34, 134, 234, 334 within the vessel. Any number of medical tasks may be performed using the overlying sheath 34, 134, 234, 334 providing a conduit to an interior of the vessel, for example, blood sampling and/or therapy delivery.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A needle assembly positionable within anatomy of a patient under visual guidance from an ultrasound system configured to direct an incident wave and receive reflected waves, said needle assembly comprising:
   an elongate body comprising:
      a distal end, and a proximal end opposite said distal end with said distal and proximal ends defining a longitudinal axis of said elongate body;
      a sidewall extending between said proximal and distal ends and comprising an outer surface opposite an inner surface defining a lumen with a portion of said lumen comprising an inner diameter; and
      a reverberation feature disposed between said proximal and distal ends with said reverberation feature comprising opposing portions of said inner surface of said sidewall defining a gap smaller than said inner diameter of said lumen,
   wherein said reverberation feature is configured to reverberate the incident wave between said opposing portions to produce the reflected waves to be received by the ultrasound system.

2. The needle assembly of claim 1, further comprising an overlying sheath disposed over at least a portion of said elongate body, said overlying sheath comprising a distal end opposite a proximal end with said distal end of said overlying sheath axially positioned proximal to said reverberation feature of said elongate body.

3. The needle assembly of claim 1, wherein said opposing portions of said reverberation feature comprise opposing planar surfaces oriented parallel to one another to define said gap.

4. The needle assembly of claim 3, wherein said opposing planar surfaces are further oriented parallel to said longitudinal axis.

5. The needle assembly of claim 3, wherein said opposing planar surfaces are further oriented angularly upward in a proximal-to-distal direction such that a midline between said opposing planar surfaces and said longitudinal axis define an acute angle.

6. The needle assembly of claim 1, wherein said opposing portions of said reverberation feature comprise opposing arcuate surfaces extending towards said longitudinal axis to define said gap.

7. The needle assembly of claim 6, wherein said opposing arcuate surfaces are positioned to at least partially overlap axially along said longitudinal axis.

8. The needle assembly of claim 1, wherein said outer surface of said elongate body is contoured to said opposing portions of said inner surface to define said sidewall of substantially constant thickness.

9. A needle assembly positionable within anatomy of a patient under visual guidance from an ultrasound system configured to direct an incident wave and receive reflected waves, said needle assembly comprising:
   an elongate body comprising:
      a beveled tip defining a distal end of said elongate body and configured to penetrate the anatomy of the patient with said beveled tip comprising a point defining an inferior aspect of said elongate body, and a heel defining a superior aspect of said elongate body;
      a proximal end opposite said distal end with said distal and proximal ends defining a longitudinal axis of said elongate body;
      a sidewall extending between said beveled tip and said proximal end and comprising an outer surface opposite an inner surface defining a lumen with a portion of said lumen comprising an inner diameter; and
      a reverberation feature comprising an upper portion of said inner surface at said superior aspect and a lower portion of said inner surface at said inferior aspect to define a gap shaped differently than said lumen with said upper and lower portions configured to cooperate to reverberate the incident wave to produce the reflected waves to be received by the ultrasound system.

10. The needle assembly of claim 9, wherein said outer surface is contoured to said inner surface to define said sidewall of substantially constant thickness.

11. The needle assembly of claim 10, wherein said sidewall further comprises an upper crimp comprising said upper portion, and a lower crimp comprising said lower portion with said upper and lower crimps axially aligned along said longitudinal axis to define said gap.

12. The needle assembly of claim 10, wherein said sidewall further comprises an upper notch comprising said upper portion, and a lower notch comprising said lower portion with said lower notch complementary to said upper notch and axially spaced apart from said upper notch along said longitudinal axis to define said gap.

13. The needle assembly of claim 10, wherein said sidewall further comprises an upper arcuate protrusion comprising said upper portion, and a lower arcuate protrusion comprising said lower portion with said lower arcuate protrusion complementary to said upper arcuate protrusion and axially spaced apart from said upper arcuate protrusion along said longitudinal axis to define said gap.

14. The needle assembly of claim 13, wherein said upper and lower arcuate protrusions are hemicylindrical in shape and oriented transverse to said longitudinal axis.

15. A needle assembly positionable within anatomy of a patient under visual guidance from an ultrasound system configured to direct an incident wave and receive reflected waves, said needle assembly comprising:
   an elongate body comprising:
      a distal end, and a proximal end opposite said distal end with said distal and proximal ends defining a longitudinal axis of said elongate body;
      a sidewall extending between said proximal and distal ends and comprising an outer surface opposite an inner surface defining a lumen on a longitudinal axis; and
      a reverberation feature disposed between said proximal and distal ends with said reverberation feature comprising said inner surface of said sidewall defining a gap that is in fluid communication with said lumen and shaped differently than with said lumen,
   wherein said reverberation feature is configured to reverberate the incident wave to produce the reflected waves to be received by the ultrasound system.

16. The needle assembly of claim 15, wherein said gap is smaller than said lumen.

17. The needle assembly of claim 15, wherein said reverberation feature comprise opposing planar surfaces oriented parallel to one another to define said gap.

18. The needle assembly of claim 17, wherein said opposing planar surfaces are further oriented parallel to said longitudinal axis.

19. The needle assembly of claim 17, wherein said opposing planar surfaces are further oriented angularly upward in a proximal-to-distal direction such that a midline between said opposing planar surfaces and said longitudinal axis define an acute angle.

\* \* \* \* \*